US012144848B2

(12) United States Patent
Quinn et al.

(10) Patent No.: US 12,144,848 B2
(45) Date of Patent: Nov. 19, 2024

(54) ARGININE DEPLETION THERAPY FOR TREATMENT OF GAMT DEFICIENCY

(71) Applicant: Aerase, Inc., Austin, TX (US)

(72) Inventors: Anthony G. Quinn, Gloucester, MA (US); Andreas Schulze, Toronto (CA); Scott W. Rowlinson, Austin, TX (US)

(73) Assignee: Immedica Pharma AB, Stockholm (SE)

(*) Notice: Subject to any disclaimer, the term of this patent is extended or adjusted under 35 U.S.C. 154(b) by 456 days.

(21) Appl. No.: 17/286,041

(22) PCT Filed: Oct. 18, 2019

(86) PCT No.: PCT/US2019/057027
§ 371 (c)(1),
(2) Date: Apr. 16, 2021

(87) PCT Pub. No.: WO2020/081994
PCT Pub. Date: Apr. 23, 2020

(65) Prior Publication Data
US 2021/0379167 A1 Dec. 9, 2021

Related U.S. Application Data

(60) Provisional application No. 62/747,837, filed on Oct. 19, 2018.

(51) Int. Cl.
*A61K 38/50* (2006.01)
(52) U.S. Cl.
CPC ...... *A61K 38/50* (2013.01); *C12Y 305/03001* (2013.01); *C12Y 305/03006* (2013.01)
(58) Field of Classification Search
CPC .................................................... A61K 38/50
See application file for complete search history.

(56) References Cited

U.S. PATENT DOCUMENTS

| | | | |
|---|---|---|---|
| 6,316,199 | B1 | 11/2001 | Vockley et al. |
| 7,229,962 | B2 | 6/2007 | Chung et al. |
| 8,398,968 | B2 | 3/2013 | Mayall |
| 8,440,184 | B2 | 5/2013 | Georgiou et al. |
| 8,679,479 | B2 * | 3/2014 | Georgiou ............... A61P 35/00 514/19.3 |
| 9,050,340 | B2 | 6/2015 | Georgiou et al. |
| 9,109,218 | B2 | 8/2015 | Cheng et al. |
| 9,382,525 | B2 | 7/2016 | Leung et al. |
| RE46,423 | E | 6/2017 | Georgiou et al. |
| 10,098,933 | B2 | 10/2018 | Georgiou et al. |
| 10,729,752 | B2 | 8/2020 | Lowe et al. |
| 11,717,562 | B2 | 8/2023 | Rowlinson et al. |
| 2002/0119554 | A1 | 8/2002 | Vockley et al. |
| 2005/0244398 | A1 | 11/2005 | Cheng et al. |
| 2008/0226617 | A1 | 9/2008 | Cheng et al. |
| 2008/0292609 | A1 | 11/2008 | Cheng et al. |
| 2009/0238813 | A1 | 9/2009 | Georgiou et al. |
| 2010/0111925 | A1 | 5/2010 | Georgiou et al. |
| 2010/0247508 | A1 | 9/2010 | Leung et al. |
| 2012/0177628 | A1 | 7/2012 | Georgiou et al. |
| 2013/0273022 | A1 | 10/2013 | Georgiou et al. |
| 2014/0023628 | A1 | 1/2014 | Leung et al. |
| 2014/0112902 | A1 | 4/2014 | Foster et al. |
| 2014/0154797 | A1 | 6/2014 | Godfrin |
| 2014/0242060 | A1 | 8/2014 | Georgiou et al. |
| 2014/0363417 | A1 | 12/2014 | Cheng et al. |
| 2015/0010522 | A1 | 1/2015 | Cheng et al. |
| 2016/0095884 | A1 | 4/2016 | Godfrin et al. |
| 2016/0161485 | A1 | 6/2016 | Chu et al. |
| 2017/0128553 | A1 | 5/2017 | Georgiou et al. |
| 2017/0191078 | A1 | 7/2017 | Zhang et al. |
| 2017/0224843 | A1 | 8/2017 | Deglon et al. |
| 2017/0240922 | A1 | 8/2017 | Gill et al. |
| 2017/0283830 | A1 | 10/2017 | Saltzman et al. |
| 2018/0177853 | A1 | 6/2018 | Lowe et al. |
| 2018/0271960 | A1 | 9/2018 | Cheng et al. |
| 2019/0000939 | A1 | 1/2019 | Georgiou et al. |
| 2019/0167770 | A1 | 6/2019 | Rowlinson et al. |
| 2020/0360493 | A1 | 11/2020 | Lowe et al. |
| 2021/0128703 | A1 | 5/2021 | Georgiou et al. |
| 2021/0189371 | A1 | 6/2021 | Rowlinson |

(Continued)

FOREIGN PATENT DOCUMENTS

| | | |
|---|---|---|
| CA | 3073116 A1 | 2/2019 |
| CN | 103184208 A | 7/2013 |

(Continued)

OTHER PUBLICATIONS

Aeglea Biotherapeutics, "Aeglea Biotherapeutics to Present Topline Data from Phase 1 Trial of Aeb11 02 for Treatment of Arginase I Deficiency at 2017 ACMG Annual Clinical Genetics Meeting," Press release, retrieved online at: ir.aegleabio.com/news-releases/news-release-details/aeglea-biotherapeutics-present-topline-data-phase-1-trial, Mar. 23, 2017, 3 pages.

Agnello et al., "Preclinical safety and antitumor activity of the arginine-degrading therapeutic enzyme pegzilarginase, a PEGylated, cobalt-substituted recombinant human arginase 1," Transl Res. Mar. 2020: 217: 11-22. Epub Dec. 27, 2019.

Allen, L. et al., eds., "Ansel's Pharmaceutical Dosage Forms and Drug Delivery Systems," 8th ed. Lippincott, 2005, excerpt, pp. 51, 53, 54, 92-94, 162-164, 169, and 182-184. 16 printed pages.

Amayreh, W. et al., "Treatment of arginase deficiency revisited: guanidinoacetate as a therapeutic target and biomarker for therapeutic monitoring," Dev Med Child Neurol. Oct. 2014; 56(10): 1021-4. Epub May 10, 2014.

Ankudinov, A. L., et al., "Real-space Multiple-scattering Calculation and Interpretation of X-ray-absorption Near-edge Structure," Physical Review B, 58: 7565-7576,1998.

Aoki S, et al., "Guanidine is a Zn(2+)-binding ligand at neutral pH in aqueous solution," J Am Chem Soc. May 15, 2002; 124(19): 5256-7.

(Continued)

*Primary Examiner* — Suzanne M Noakes
(74) *Attorney, Agent, or Firm* — COOLEY LLP

(57) ABSTRACT

Methods and compositions therefor of treating GAMT deficiency or guanidino acetate (GAA) toxicity in a subject comprising administration of an arginine depleting enzyme. An therapeutic formulation can include an arginase, an arginine deiminase or a combination thereof and optionally other compounds, and can be adapted for intravenous or subcutaneous administration to a subject.

35 Claims, 6 Drawing Sheets

Specification includes a Sequence Listing.

(56) References Cited

U.S. PATENT DOCUMENTS

| | | |
|---|---|---|
| 2024/0009283 A1 | 1/2024 | Georgiou et al. |
| 2024/0009284 A1 | 1/2024 | Rowlinson et al. |

FOREIGN PATENT DOCUMENTS

| | | |
|---|---|---|
| EP | 1803465 A1 | 7/2007 |
| EP | 2799539 A1 | 11/2014 |
| JP | H02117383 A | 5/1990 |
| WO | WO-03063780 A2 | 8/2003 |
| WO | WO-2004001048 A1 | 12/2003 |
| WO | WO-2010051533 A2 | 5/2010 |
| WO | WO-2010124547 A1 | 11/2010 |
| WO | WO-2011008495 A2 | 1/2011 |
| WO | WO-2012061015 A2 | 5/2012 |
| WO | WO-2012085793 A1 | 6/2012 |
| WO | WO-2015164743 A2 | 10/2015 |
| WO | WO-2016033555 A1 | 3/2016 |
| WO | WO-2017192449 A1 | 11/2017 |
| WO | WO-2018032020 A1 | 2/2018 |
| WO | WO-2019035935 A1 | 2/2019 |
| WO | WO-2019113157 A1 | 6/2019 |
| WO | WO-2019228510 A1 | 12/2019 |
| WO | WO-2020081994 A1 | 4/2020 |
| WO | WO-2021041904 A1 | 3/2021 |
| WO | WO-2021202957 A1 | 10/2021 |
| WO | WO-2021257523 A1 | 12/2021 |
| WO | WO-2023201228 A1 | 10/2023 |

OTHER PUBLICATIONS

Ascierto, P. A., et al., "Pegylated arginine deiminase treatment of patients with metastatic melanoma: results from phase I and II studies," J Clin Oncol. Oct. 20, 2005; 23(30): 7660-8.

Ash, D. E., "Structure and function of Arginases," J Nutr. Oct. 2004; 134(10 Suppl): 2760S-2764S; discussion 2765S-2767S. 5 printed pages.

ATS Committee on Proficiency Standards for Clinical Pulmonary Function Laboratories, "ATS Statement Guidelines for the Six-Minute Walk," Am J Respir Crit Care Med. Jul. 1, 2002; 166(1): 111-7.

Auld, D. S. & Vallee, B. L., "Kinetics of Carboxypeptidase A. The PH Dependence of Tripeptide Hydrolysis Catalyzed by Zinc, Cobalt, and Manganese Enzymes," Biochemistry, 9: 4352-4359, 1970.

Aulton, M., ed., "Pharmaceutics: The Design and Manufacture of Medicines," Elsevier, 2007, excerpt, pp. 4, 5, 286, and 324. 5 printed pages.

Badarau A, et al., "The Variation of Catalytic Efficiency of Bacillus Cereus Metallo-beta-lactamase with Different Active Site Metal Ions," Biochemistry. Sep. 5, 2006; 45(35): 10654-66.

Badeaux et al., "Arginase Therapy Combines Effectively with Immune Checkpoint Blockade or Agonist Anti-0X40 Immunotherapy to Control Tumor Growth," Cancer Immunology Research, vol. 9, No. 4, Apr. 1, 2021 (Apr. 1, 2021), pp. 415-429.

Bansal, V., et al., "Arginine Availability, Arginase, and the Immune Response," Curr Opin Clin Nutr Metab Care. Mar. 2003; 6(2): 223-8.

Beale R N & Croft D., "A Sensitive Method for the Colorimetric Determination of Urea," J. Clin. Pathol., 14: 418-24, 1961.

Becht H et al., "Induction of an Arginine-rich Component during Infection with Influenza Virus," Journal of General Virology, vol. 4, No. 2, Mar. 1, 1969, pp. 215-220.

Bewley et al., "Crystal Structures of Bacillus Caldovelox Arginase in Complex with Substrate and Inhibitors Reveal New Insights into Activation, Inhibition and Catalysis in the Arginase Superfamily," Structure, 7: 435-448, 1999.

Bicker and Thompson "The protein arginine deiminases (PADs): Structure, Function, Inhibition, and Disease," Biopolymers. Feb. 2013; 99(2): 155-163.

Bickmore et al., "Bond-valence Methods for Pka Prediction. II. Bond-valence, Electrostatic, Molecular Geometry, and Solvation Effects," Geochimica Et Cosmochimica Acta, 70: 4057-4071, 2006.

Braissant, "GAMT deficiency: 20 years of a treatable inborn error of metabolism," Mol Genet Metab. Jan. 2014; 111(1): 1-3. Epub Nov. 10, 2013.

Burrage, L.C. et al., "Human recombinant arginase enzyme reduces plasma arginine in mouse models of arginase deficiency," Human Molecular Genetics, vol. 24, No. 22, 2015, pp. 6417-6427.

Caldwell, R. William et al., "Arginase: A Multifaceted Enzyme Important in Health and Disease," Physiol Rev. Apr. 1, 2018; 98(2): 641-665.

Cama et al., "Structural and Functional Importance of First-shell Metal Ligands in the Binuclear Manganese Cluster of Arginase 1," Biochemistry. Jul. 1, 2003; 42(25): 774858. 11 pages.

Carvajal et al., "Consequences of Mutations of Metal Ligands in Human Liver Arginase 1," Molecular Biology of the Cell, 13: 546A, 2002. 1 page.

Carvajal et al., Interaction of Arginase with Metal Ions: Studies of the Enzyme from Human Liver and Comparison with Other Arginases, Camp Biochem Physiol B Biochem Mol Bioi, 112: 153-159, 1995.

Carvalho, D.R., et al., "Clinical features and neurologic progression of hyperargininemia," Pediatr. Neural., 46(6): 369-74 (2012).

Cavalli et al., "Mutagenesis of Rat Liver Arginase Expressed in Escherichia coli: Role of Conserved Histidines," Biochemistry. Sep. 6, 1994; 33(35): 10652-7.

Cellarier et al., "Methionine Dependency and Cancer Treatment," Cancer Treat. Rev., 29: 489-499, 2003.

Chaberek et al., "Stability of Metal Chelates. II. B-hydroxyethyliminodiacetic Acid," J Am. Chem. Soc., 74: 5057-60, 1952.

Cheng et al., "Enhanced hepatocyte growth factor signaling by type II transforming growth factor-beta receptor knockout fibroblasts promotes mammary tumorigenesis," Cancer Res., 67: 4869-4877, 2007.

Cheng et al., "Pegylated recombinant human arginase (rhArg-peg5,000mw) inhibits the in vitro and in vivo proliferation of human hepatocellular carcinoma through arginine depletion," Cancer Res. Jan. 1, 2007; 67(1): 309-17.

Cheng et al., "Remission of hepatocellular carcinoma with arginine depletion induced by systemic release of endogenous hepatic arginase due to transhepatic arterial embolisation, augmented by high-dose insulin: arginase as a potential drug candidate for hepatocellular carcinoma," Cancer Lett. Jun. 16, 2005; 224(1): 67-80. Epub Dec. 25, 2004.

Christianson and Cox, "Catalysis by metal-activated hydroxide in zinc and manganese metalloenzymes," Annu Rev Biochem. 1999: 68: 33-57.

Christianson and Fierke, "Carbonic anhydrase: evolution of the zinc binding site by nature and by design," Ace. Chem. Res., 29: 331-339, 1996.

Colleluori et al., "Expression, purification, and characterization of human type II arginase," Arch Biochem Biophys. May 1, 2001; 389(1): 135-43.

Colleluori et al. "Probing the role of the hyper-reactive histidine residue of Arginase," Arch Biochem Biophys. Dec. 1, 2005; 444(1):15-26. Epub Oct. 13, 2005. 12 pages.

Compaan, D.M. et al., "The crystal structure of the costimulatory OX40-OX40L complex," Structure. Aug. 2006; 14(8): 1321-30.

Das, S. C., et al., "The Highly Conserved Arginine Residues at Positions 76 through 78 of Influenza A Virus Matrix Protein M1 Play an Important Role in Viral Replication by Affecting the Intracellular Localization of M1", Journal of Virology, vol. 86, No. 3, Nov. 16, 2011, pp. 1522-1530.

Deignan et al., "Increased plasma and tissue guanidine compounds in a mouse model of hyperargininemia," Mol. Genet. Metab. 93: 172-178, 2008.

Di Costanzo et al., "Stereochemistry of guanidine-metal interactions: implications for L-arginine-metal interactions in protein structure and function," Proteins. Nov. 15, 2006; 65(3): 637-42.

Dillon et al., "Biochemical characterization of the arginine degrading enzymes arginase and arginine deiminase and their effect on nitric oxide production," Med Sci Monit. Jul. 2002; 8(7): BR248-53.

(56) References Cited

OTHER PUBLICATIONS

Dinndorf et al., "FDA Drug Approval Summary: Pegaspargase (Oncaspar) for the First-line Treatment of Children with Acute Lymphoblastic Leukemia All)," Oncologist, 12: 991-998, 2007.
Dowling et al., "Evolution of the arginase fold and functional diversity," Cell Mol Life Sci. Jul. 2008; 65(13): 2039-55.
Downs, Stephen, "The Berg Balance Scale," J Physiother. Jan. 2015; 61(1): 46. Epub Dec. 1, 2014. 1 page.
Durante et al., "Arginase: a critical regulator of nitric oxide synthesis and vascular function," Clin Exp Pharmacol Physiol. Sep. 2007; 34(9): 906-11.
Dwight L. McKee et al., "Candidate drugs against SARS-CoV-2 and COVID-19," Pharmacological Research., vol. 157, Jan. 1, 2020 (Jan. 1, 2020), p. 104859.
Enright et al., "Reference equations for the six-minute walk in healthy adults," Am. J. Respir. Grit. Care Med., 1998 158(5 Pt 1): 1384-1387.
Ensor et al., "Pegylated arginine deiminase (Adi-SS PEG20,000 mw) inhibits human melanomas and hepatocellular carcinomas in vitro and in vivo," Cancer Res. Oct. 1, 2002; 62(19): 5443-50.
Feun et al., "Clinical trial of CP 1-11 and VM-26/VP-16 for patients with recurrent malignant brain tumors," J Neurooncol. Apr. 2007; 82(2): 177-81. Epub Oct. 19, 2006.
Final Office Action for U.S. Appl. No. 13/863,448 dated Oct. 22, 2014, 6 pages.
Final Office Action for U.S. Appl. No. 16/210,248 dated Apr. 6, 2021, 8 pages.
Fletcher et al., "I-Arginine depletion blunts antitumor T-cell responses by inducing myeloid-derived suppressor cells," Cancer Res. Jan. 15, 2015; 75(2): 275-83. Epub Nov. 18, 2014.
Fultang, L., et al., "Molecular Basis and Current Strategies of Therapeutic Arginine Depletion for Cancer", International Journal of Cancer, Val. 139, No. 3, Apr. 15, 2016 (Apr. 15, 2016), pp. 501-509.
Geiger et al., "Six-minute walk test in children and adolescents," J Pediatr. Apr. 2007; 150(4): 395-9, 399.e1-2. 6 pages.
Gill and Von Hippel, "Calculation of protein extinction coefficients from amino acid sequence data," Anal Biochem. Nov. 1, 1989; 182(2): 319-26.
Glazer, E., et al., "Bioengineered Human Arginase I with Enhanced Activity and Stability Controls Hepatocellular and Pancreatic Carcinoma Xenografts," Translational Oncology, 2011, 4(3): 138-146.
Grimes et al., "Arginine depletion as a therapeutic approach for patients with COVID-19," International Journal of Infectious Diseases, International Society for Infectious Diseases, Hamilton, CA, vol. 102, 4 Nov. 4, 2020, pp. 566-570.
Haberle et al., "Suggested guidelines for the diagnosis and management of urea cycle disorders," Orphanet. J. Rare Dis., 2012 7: 32.
Han et al., "Synthesis and evaluation of alternative substrates for arginase," Bioorg Chern, 30: 81-94, 2002.
Haraguchi et al., "Molecular cloning and nucleotide sequence of cDNA for human liver arginase," Proc Natl Acad Sci USA. Jan. 1987; 84(2): 412-5.
Harris et al., "Pegylation: a novel process for modifying pharmacokinetics," Clin Pharmacokinet. 2001; 40(7): 539-51.
He et al., "Aminoguanidinium hydrolysis effected by a hydroxobridged dicobalt (II) complex as a functional model for arginase and catalyzed by mononuclear cobalt (II) complexes," J. Am. Chern. Soc., 120: 105-113, 1998.
Hernandez, C. P. et al., "Pegylated arginase I: a potential therapeutic approach in T-ALL," Blood. Jun. 24, 2010; 115(25): 5214-21. Epub Apr. 20, 2010.
Holtsberg et al., "Poly(ethylene Glycol) Peg) Conjugated Arginine Deiminase: Effects of Peg Formulations on Its Pharmacological Properties," Journal of Controlled Release, 80: 259-271, 2002.
Ikemoto et al., "Expression of Human Liver Arginase in *Escherichia coli*: Purification and Properties ofthe Product," Biochem. J., 270: 697-703, 1990.

International Preliminary Report on Patentability for International Application No. PCT/US2018/063982, mailed Jun. 18, 2020, 9 pages.
International Preliminary Report on Patentability for International Application No. PCT/US2021/025509, mailed Oct. 13, 2022, 9 pages.
International Preliminary Report on Patentability for International Application No. PCT/US2021/037362, mailed Dec. 29, 2022, 8 pages.
International Preliminary Report on Patentability for International Patent Application No. PCT/US2017/050816, mailed Feb. 21, 2019. 11 pages.
International Preliminary Report on Patentability for PCT/US2019/062471 dated May 25, 2021, 7 pages.
International Preliminary Report on Patentability issued for International Application No. PCT/US2019/057027, mailed Apr. 29, 2021, 8 pages.
International Preliminary Report on Patentability Issued in International Application No. PCT/US2010/040205, mailed Jan. 12, 2012. 7 pages.
International Preliminary Report on Patentability received for International Application No. PCT/US2020/048536, mailed Mar. 10, 2022. 14 pages.
International Search Report and Written Opinion for International Application No. PCT/US2009/062969, mailed Jun. 17, 2010. 14 pages.
International Search Report and Written Opinion for International Application No. PCT/US2010/040205, mailed Mar. 25, 2011. 11 pages.
International Search Report and Written Opinion for International Application No. PCT/US2017/050816. mailed Dec. 28, 2017, 17 pages.
International Search Report and Written Opinion for International Application No. PCT/US2018/063982, mailed Feb. 28, 2019, 16 pages.
International Search Report and Written Opinion for International Application No. PCT/US2019/057027, mailed Apr. 2, 2020, 11 pages.
International Search Report and Written Opinion for International Application No. PCT/US2020/048536 dated Feb. 22, 2021, 22 pages.
International Search Report and Written Opinion for International Application No. PCT/US2021/021148 Jul. 28, 2021, 12 pages.
International Search Report and Written Opinion for International Application No. PCT/US2021/025509, mailed on Jul. 21, 2021, 13 pages.
International Search Report and Written Opinion for International Application No. PCT/US2021/037362, mailed on Sep. 24, 2021, 11 pages.
International Search Report and Written Opinion for International Application No. PCT/US2023/065630 dated Jul. 28, 2023, 9 pages.
Invitation to Pay additional fees received for International Application No. PCT/US2020/048536, mailed Nov. 5, 2020. 10 pages.
Irving and Williams, "Order of stability of metal complexes," Nature, 162: 746-747, 1948.
Izzo et al., "Pegylated arginine deiminase lowers hepatitis C viral titers and inhibits nitric oxide synthesis", J Gastroenterol Hepatol. Jan. 2007; 22(1): 86-91.
Jefferis, "Antibody therapeutics: isotype and glycoform selection," Expert Opin Biol Ther. Sep. 2007; 7(9): 1401-13.
Jenkinson, Christopher P., et al., "Comparative properties of arginases," Comparative Biochemistry and Physiology Part B: Biochemistry and Molecular Biology (1996); 114(1): 107-132.
Jeon, H., et al., "Structure and Cancer Immunotherapy of the 87 Family Member B7x," Cell Reports, 2014, 9(3): 1089-1098.
Kalnine el al., Database GenBank Accession No. BT0199354, "Synthetic construct *Homo sapiens* arginase, type II mRNA, partial cds," NCBI Protein DB[online], Oct. 28, 2004 [retrieved on Aug. 16, 2013], URL: http://www.ncbi.nim.nih.~ov/nuccore/BT019935. 2 printed pages.
Kang J. et al., "Emerging PEGylated drugs," Expert Opin Emerg Drugs. Jun. 2009; 14(2): 363-80.

(56) References Cited

OTHER PUBLICATIONS

Katusic, Z., "Mechanisms of endothelial dysfunction induced by Aging: Role of Arginase 1," Circ Res. Sep. 28, 2007; 101(7): 640-1.
Kelly et at., "Arginine deiminase PEG20 inhibits growth of small cell lung cancers lacking expression of argininosuccinate synthetase," Br J Cancer. Jan. 17, 2012; 106(2): 324-32. Epub Dec. 1, 2011.
Khangulov et al., "L-arginine binding to liver arginase requires proton transfer to gateway residue His141 and coordination of the guanidinium group to the dimanganese(II,II) center," Biochemistry. Jun. 9, 1998; 37(23): 8539-50.
Knipp and Vasak, "A colorimetric 96-well microtiter plate assay for the determination of enzymatically formed citrulline," Anal Biochem. Nov. 15, 2000; 286(2): 257-64.
Kuhn et al., "pH-sensitive control of arginase by Mn(II) ions at submicromolar concentrations," Arch Biochem Biophys. Apr. 1991; 286(1): 217-21.
Lam, T. L., et al., "Recombinant human arginase inhibits proliferation of human hepatocellular carcinoma by inducing cell cycle arrest," Cancer Lett. May 8, 2009; 277(1): 91-100. Epub Jan. 12, 2009.
Lamb, J. & Wheatley, D. N., "Single Amino Acid Arginine) Deprivation Induces GI Arrest Associated with Inhibition of Cdk4 Expression in Cultured Human Diploid Fibroblasts," Exp Cell Res. Mar. 15, 2000; 255(2): 238-49.
Lambert et al., "Hyperargininemia: intellectual and motor improvement related to changes in biochemical data," J Pediatr. Mar. 1991;118(3): 420-4.
Lastwika, K.J., et al., "Control of PD-L1 Expression by Oncogenic Activation of the AKT-mTOR Pathway in Non-Small Cell Lung Cancer," Cancer Research, vol. 76, No. 2, Dec. 4, 2015, pp. 227-238.
Lavulo et al., "Subunit-subunit interactions in trimeric arginase. Generation of active monomers by mutation of a single amino acid," J Biol Chem. Apr. 27, 2001; 276(17): 14242-8. Epub Jan. 24, 2001.
Lesterhuis, W.J., "Network analysis of immunotherapy-induced regressing tumours identifies novel synergistic drug combinations," Scientific Reports, Jul. 2015, 5: 12298. 11 pages printed.
Linch, S. N., et al., "OX40 Agonists and Combination Immunotherapy: Putting the Pedal to the Metal," Front Oncol. Feb. 16, 2015: 5: 34. eCollection 2015. 14 pages.
Lopez et al., "Insights into the interaction of human arginase II with substrate and manganese ions by site-directed mutagenesis and kinetic studies. Alteration of substrate specificity by replacement of Asn149 with Asp," FEBS J. Sep. 2005; 272(17): 4540-8.
Luneburg, N. et al., "Reference intervals for plasmaL-arginine and the L-arginine:asymmetric dimethylarginine ratio in the Framingham Offspring Cohort," J Nutr. Dec. 2011; 141(12): 2186-90. Epub Oct. 26, 2011.
Izzo et al., "Pegylated arginine deiminase treatment of patients with unresectable hepatocellular carcinoma: results from phase 1/11 studies", J. Clin. Oncol., 22: 1815-1822, 2004.
Malumbres & Barbacid, "To Cycle or Not to Cycle: a Critical Decision in Cancer," Nat Rev Cancer. Dec. 2001; 1(3): 222-31.
Marescau et al., "Guanidino compound analysis as a complementary diagnostic parameter for hyperargininemia: follow-up of guanidino compound levels during therapy," Pediatr Res. Mar. 1990; 27(3): 297-303.
Marescau et al., "The pathobiochemistry of uremia and hyperargininemia further demonstrates a metabolic relationship between urea and guanidinosuccinic acid," Metabolism. Sep. 1992; 41(9): 1021-4.
Market, Marisa et al., "Flattening the COVID-19 Curve With Natural Killer Cell Based Immunotherapies," Frontiers in Immunology, vol. 11, Jan. 1, 2020 (Jan. 1, 2020), p. 1512.
McGee et al., "Purification and characterization of Helicobacter pylori arginase, RocF: unique features among the arginase superfamily," Eur J Biochem. May 2004; 271(10): 1952-62.
Mercimek-Mahmutoglu et al., "A pilot study to estimate incidence of guanidinoacetate methyltransferase deficiency in newborns by direct sequencing of the GAMT gene," Gene. Jan. 1, 2016; 575(1): 127-31. Epub Aug. 28, 2015.
Mora et al., "Implications of the S-shaped domain in the quaternary structure of human arginase," Biochemica. Biophysica. Acta., 1476: 181-90, 2000.
Murch et al., "Common determinants of severe Covid-19 infection are explicable by SARS-CoV-2 secreted glycoprotein interaction with the CD33-related Siglecs, Siglec-3 and Siglec-5/14," Med Hypotheses. Nov. 2020: 144: 110168. Epub Aug. 7, 2020. 7 pages.
Newville, M., "IFEFFIT: interactive XAFS analysis and FEFF fitting," J Synchrotron Radiat. Mar. 1, 2001; 8(Pt 2): 322-4.
Ni et al., "Arginine deiminase, a potential anti-tumor drug," Cancer Lett. Mar. 8, 2008; 261(1): 1-11. Epub Jan. 7, 2008.
Non-Final Office Action for U.S. Appl. No. 15/270,955 dated Aug. 10, 2017, 12 pages.
Notice of Allowance Issued in Canadian Patent Application No. 2,742,497, dated Aug. 12, 2019. 1 page.
Oeffinger et al., "Outcome tools used for ambulatory children with cerebral palsy: responsiveness and minimum clinically important differences," Dev Med Child Neurol. Dec. 2008; 50(12): 918-25.
Office Action and Search Report for Chinese Application No. CN201880079119.9 dated May 27, 2023, with English translation, 11 pages.
Office Action for Australian Application No. AU20170310541 dated Sep. 8, 2023, 5 pages.
Office Action for Japanese Application No. JP20200531164 mailed Jul. 25, 2023, with English translation, 4 pages.
Office Action issued in Canadian Patent Application No. 2,742,497, dated Apr. 20, 2018. 3 pages.
Office Action Issued in Canadian Patent Application No. 2,742,497, dated Oct. 30, 2018. 3 pages.
Office Action issued in European Patent Application No. 16163214.6, dated Jun. 12, 2018. 5 pages.
Office Communication issued in European Patent Application No. 09824219.1, dated Aug. 27, 2013. 5 pages.
Office Communication issued in Japanese Patent Application No. 2011-534855, dated Aug. 22, 2013. (English translation of Japanese text). 11 pages.
Office Communication issued in Japanese Patent Application No. 2011-534855, dated Jun. 5, 2014. (English translation of Japanese text). 5 pages.
Office Communication issued in U.S. Appl. No. 13/863,448, dated Feb. 24, 2014. 6 pages.
Office Communication issued in U.S. Appl. No. 13/863,448, dated Jun. 19, 2014. 24 pages.
Office Communication issued in U.S. Appl. No. 12/610,685, dated Aug. 26, 2011. 9 pages.
Office Communication issued in U.S. Appl. No. 12/610,685, dated Dec. 8, 2011. 22 pages.
Office Communication issued in U.S. Appl. No. 12/610,685, dated May 24, 2012. 14 pages.
Palacios et al., "Studies on the advent of ureotelism. The effects of bivalent cations on the capacity of the hepatic arginase of the Mexican axolotl to hydrolyse endogenous arginine," Biochem J. Sep. 1969; 114(3): 449-54.
Periyannan et al., "Sequential binding of cobalt(II) to metallo-beta-lactamase CcrA," Biochemistry. Jan. 31, 2006; 45(4): 1313-20.
Perrin, "421. The hydrolysis of manganese (II) ion," Journal of the Chemical Society, pp. 2197-2200, 1962.
Prasad et al., "Argininemia: a treatable genetic cause of progressive spastic diplegia simulating cerebral palsy: case reports and literature review," J Child Neurol. Aug. 1997; 12(5): 301-9.
Ratilla et al., "Terminal and new bridging coordination of methylguanidine, arginine, and canavanine to platinum (II). The first crystallographic study of bonding between a transition metal and a Quanidine ligand," InorQanic Chemistry, 29: 918-926, 1990.
Reczkowski and Ash, "Rat liver arginase: kinetic mechanism, alternate substrates, and inhibitors," Arch. Biochem. Biophys., 312: 31-7, 1994.
Rehner et al., "Effect of manganese cobalt and nickel on the activity of liver arginase in-vitro and in-vivo," Medizin und Ernaehrung, 11 (2): 32-35, 1970. With English summary. 4 pages.
Robins and Shields, "Partial purification of bovine liver arginase," Archives of Biochemistry and Biophysics, 62: 55-62, 1956. (Abstract only). 1 page.

(56) References Cited

OTHER PUBLICATIONS

Rodriguez et al., "Arginine Metabolism in Myeloid Cells Shapes Innate and Adaptive Immunity," Front Immunol. Feb. 7, 2017: 8: 93. eCollection 2017. 12 pages.

Roopenian and Akilesh, "FcRn: the neonatal Fc receptor comes of age," Nat Rev Immunol. Sep. 2007; 7(9): 715-25. Epub Aug. 17, 2007.

Sabio et al., "Glu-256 is a main structural determinant for oligomerisation of human arginase I," FEBS Lett. Jul. 20, 2001; 501(2-3): 161-5.

Santhanam et al., "Inducible NO synthase dependent S-nitrosylation and activation of arginase1 contribute to age-related endothelial dysfunction," Circ Res. Sep. 28, 2007; 101(7): 692-702. Epub Aug. 17, 2007.

Sarkissian and Gamez, "Phenylalanine ammonia lyase, enzyme substitution therapy for phenylketonuria, where are we now?" Mol Genet Metab. Dec. 2005: 86 Suppl 1: S22-6. Epub Sep. 13, 2005.

Savoca et al., "Cancer therapy with chemically modified enzymes. II. The therapeutic effectiveness of arginase, and arginase modified by the covalent attachment of polyethylene glycol, on the taper liver tumor and the L5178Y murine leukemia," Cancer Biochem Biophys. Sep. 1984; 7(3): 261-8.

Schierhorn et al., "Influenza A Virus Virulence Depends on Two Amino Acids in the N-Terminal Domain of Its NS1 Protein to Facilitate Inhibition of the RNA-Dependent Protein Kinase PKR," Journal of Virology, vol. 91, No. 10, May 15, 2017. 18 pages.

Schlune et al., "Hyperargininemia due to arginase I deficiency: the original patients and their natural history, and a review of the literature," Amino Acids. Sep. 2015; 47(9): 1751-62. Epub Jun. 27, 2015.

Schrover et al., "Minimal clinically important difference for the 6-min walk test: literature review and application to Morquio A syndrome," Orphanet J Rare Dis. Apr. 26, 2017; 12(1): 78. 11 pages.

Scolnick et al., "Altering the binuclear manganese cluster of Arginase diminishes thermostability and catalytic function," Biochemistry. Aug. 26, 1997; 36(34): 10558-65.

Scott et al., "Single amino acid (arginine) deprivation: rapid and selective death of cultured transformed and malignant cells," Br J Cancer. Sep. 2000; 83(6): 800-10.

Seely et al., "Making Site-specific Pegylation Work," BioPharm International 03-012005, vol. 18, Issue 3. Published Feb. 28, 2005. 9 printed pages.

Segawa et al., "A long-term survival case of arginase deficiency with severe multicystic white matter and compound mutations," Brain Dev. Jan. 2011; 33(1): 45-8. Epub Apr. 24, 2010.

Segel, "Enzyme Kinetics: behavior and analysis of rapid equilibrium and steady state enzyme systems," New York, John Wiley and Sons, Inc., pp. 914-917, 1975.

Shen et al., "Modulation of Arginine Metabolic Pathways as the Potential Anti-tumor Mechanism of Recombinant Arginine Deiminase," Cancer Lett., 231: 30-35, 2006.

Simmons et al., "Expression of full-length immunoglobulins in *Escherichia coli*: rapid and efficient production of aglycosylated antibodies," J Immunol Methods. May 1, 2002; 263(1-2): 133-47.

Spector et al., "Properties of fetal and adult red blood cell arginase: a possible prenatal diagnostic test for arginase deficiency," Am J Hum Genet. Jan. 1980; 32(1): 79-87.

Stemmler et al., "EXAFS comparison of the dimanganese core structures of manganese catalase, arginase, and manganese-substituted ribonucleotide reductase and hemerythrin," Biochemistry. Aug. 12, 1997; 36(32): 9847-58.

Stern et al., "Guanidinoacetate methyltransferase (GAMT) deficiency: a rare but treatable epilepsy," Pract Neurol. Jun. 2017; 17(3): 207-211. Epub Jan. 24, 2017.

Stockler-Ipsiroglu et al., "Guanidinoacetate methyltransferase (GAMT) deficiency: outcomes in 48 individuals and recommendations for diagnosis, treatment and monitoring," Mol Genet Metab. Jan. 2014; 111(1): 16-25. Epub Nov. 7, 2013.

Stone E. et al. "Strategies for Optimizing the Serum Persistence of Engineered Human Arginase I for Cancer Therapy," J Control Release. Feb. 28, 2012; 158(1): 1719. Epub Oct. 6, 2011.

Stone E M., et al., "Replacing Mn2+ with Co2+ in Human Arginase I Enhances Cytotoxicity Towards L-1arginine Auxotrophic Cancer Cell Lines," Acs Chern Bioi. Mar. 19, 2010; 5(3): 333-342.

Stone et al., "Engineering Human Arginase I as a Novel Cancer Therapeutic Agent," Retrieved from the Internet at http://aiche.conefx.com/aiche/09icbe/preliminaryprogram/abstract_143378.htm, retrieved on Feb. 29, 2012, dated Sep. 6, 2008.

Storr & Burton, "The Effects of Arginine Deficiency on Lymphoma Cells," Br. J. Cancer, 30: 50-59, 1974.

Supplementary European Search Report and Search Opinion issued in European Application No. 09824219.1, mailed May 31, 2012. 7 pages.

Tao and Morrison, "Studies of aglycosylated chimeric mouse-human IgG. Role of carbohydrate in the structure and effector functions mediated by the human IgG constant region," J Immunol. Oct. 15, 1989; 143(8): 2595-601.

Tate et al., "Effect of arginase II on L-arginine depletion and cell growth in murine cell lines of renal cell carcinoma," J Hematol Oncol. Sep. 25, 2008: 1: 14. 10 pages.

Topal et al., "Mitochondrial Arginase II Modulates Nitric-Oxide Synthesis through Nonfreely Exchangeable L-Arginine Pools in Human Endothelial Cells," J Pharmacol Exp Ther. Sep. 2006; 318(3): 1368-74. Epub Jun. 26, 2006.

Tsui et al., "Pegylated Derivatives of Recombinant Human Arginase rhargl) for Sustained in Vivo Activity in Cancer Therapy: Preparation, Characterization and Analysis of Their Pharmacodynamics in Vivo and in Vitro and Action upon Hepatocellular Carcinoma Cell HCC)," Cancer Cell Int. Apr. 17, 2009: 9: 9. 13 pages.

Uchino, T., et al., "Molecular basis of Phenotypic Variation in patients with argininemia," Hum Genet. Sep. 1995; 96(3): 255-60.

U.S. Department of Health and Human Services, Food and Drug Administration Center for Drug Evaluation and Research (CDER), "Guidance for Industry Estimating the Maximum Safe Starting Dose in Initial Clinical Trials for Therapeutics in Adult Healthy Volunteers," Jul. 2005, 30 pages.

Viau, et al., "Evidence-Based Treatment of Guanidinoacetate Methyltransferase (GAMT) Deficiency," Mol Genet Metab. Nov. 2013; 110(3): 255-62. Epub Sep. 8, 2013.

Vigdorovich, V., et al., "Structure and T Cell Inhibition Properties of 87 Family Member, B7-H3," Structure, 2013, 21 (5): 707-717.

Vockley et al., "Loss of functional mutations in conserved regions of the human arginase I gene," Biochemical and Molecular Medicine, 59: 44-51, 1996.

Webb, "SIXPACK: a graphical user interface for XAS analysis using IFEFFIT," Physica Scripta, 115: 1011-1014, 2005.

Wetzler et al., "Effective Asparagine Depletion with Pegylated Asparaginase Results in Improved Outcomes in Adult Acute Lymphoblastic Leukemia: Cancer and Leukemia Group B Study 9511," Blood, 109: 4164-4167, 2007.

Wheatly and Campbell, "Arginine catabolismliver extracts and cancer," Pathol. Oncol. Res., 8: 18-25, 2002.

Wheatley, "Arginine deprivation and metabolomics: important aspects of intermediary metabolism in relation to the differential sensitivity of normal and tumour cells," Semin Cancer Biol. Aug. 2005; 15(4): 247-53.

Wheatley et al., "Single Amino Acid Arginine) Restriction: Growth and Death of Cultured Hela and Human Diploid Fibroblasts," Cell Physiol Biochem. 2000; 10(1-2): 37-55.

Witalison et al., "Protein Arginine Deiminases and Associated Citrullination: Physiological Functions and Diseases Associated with Dysregulation," Curr Drug Targets. 2015; 16(7): 700-710.

Wu, G. et al., "Arginine metabolism: nitric oxide and beyond," Biochem J. Nov. 15, 1998; 336 (Pt 1) (Pt 1):1-17.

Wyse et al., "In vitro stimulation of oxidative stress in cerebral cortex of rats by the guanidino compounds accumulating in hyperargininemia," Brain Res. Dec. 27, 2001; 923(1-2): 50-7.

Yau et al. "A phase 1 dose-escalating study of pegylated recombinant human arginase 1 (Peg-rhArg1) in patients with advanced hepatocellular carcinoma," Invest New Drugs. Feb. 2013; 31(1): 99-107. Epub Mar. 17, 2012.

(56) References Cited

OTHER PUBLICATIONS

Ye et al., "Targeting Ornithine Decarboxylase by α-Difluoromethylornithine Inhibits Tumor Growth by Impairing Myeloid-Derived Suppressor Cells," Journal of Immunology, 2016, 196: 915-923; published online Dec. 9, 2015.

Yoon et al., "Renal cell carcinoma does not express argininosuccinate synthetase and is highly sensitive to arginine deprivation via arginine deiminase," Int. J. Cancer, 120: 897-905, 2006.

Yu et al., "PD-1 blockade attenuates immunosuppressive myeloid cells due to inhibition of CD47/SIRPα axis in HPV negative head and neck squamous cell carcinoma," Oncotarget, 2015, 6: 42067-42079.

Zarganes-Tzitzikas, T., et al., "Inhibitors of programmed cell death1 (PD-1): a patent review (2010-2015)," Expert Opinion on Therapeutic Patents, 2016, 26(9): 973977.

Zhang et al., "The cyanobacterial ornithine-ammonia cycle involves an arginine dihydrolase," Nat Chem Biol. Jun. 2018; 14(6): 575-581. Epub Apr. 9, 2018.

Zori, Roberto, et al., "Initial Results of a Phase 1 Open Label Study of AEB1102 Enzyme Replacement Therapy in Adult Patients with Arginase I Deficiency," Aeglea BioTherapeutics, Mar. 2017. 1 page.

Zori, R.T., "Once Weekly Intravenous Administration of Pegzilarginase Produces Marked and Sustained Reductions in Plasma Arginine Levels in Adults with Arginase 1 Deficiency: Early Results from a Phase 1/2 Open-label Study of Pegzilarginase," Molecular Genetics and Metabolism, 2018, Embase Database: Xp002788803, Database Accession No. Emb-622060654 [Abstract]. 1 page.

\* cited by examiner

SEQUENCE LISTING

```
<160> NUMBER OF SEQ ID NOS: 4

<210> SEQ ID NO 1
<211> LENGTH: 1044
<212> TYPE: DNA
<213> ORGANISM: Artificial Sequence
<220> FEATURE:
<223> OTHER INFORMATION: Synthetic sequence

<400> SEQUENCE: 1
gatataccat gggttcttct caccatcatc accaccacag ctctggcgag aacctgtact      60
```

| | |
|---|---|
| tccagtctgc gaagagccgt acgatcggca ttattggtgc gccgttctct aaaggtcagc | 120 |
| cacgcggtgg tgtggaagag ggtccgacgg ttctgcgtaa ggccggttta ttagaaaagc | 180 |
| tgaaagagca ggagtgcgac gttaaggact acggtgactt accattcgcg gacatcccga | 240 |
| atgatagccc gttccaaatc gttaagaatc cgcgctctgt gggtaaagca agcgagcagt | 300 |
| tagcaggtaa ggtggccgag gtcaagaaaa acggtcgtat tagcctggtt ttaggcggtg | 360 |
| atcatagctt agcaattggc tctatctctg gtcatgcccg tgtgcaccca gatttaggtg | 420 |
| tcatttgggt tgacgcccat acggatatca atacgccatt aacgaccacc agcggcaatc | 480 |
| tgcatggcca gccggttagc ttcttactga aggagctgaa gggtaaaatt ccagatgttc | 540 |
| cgggctttag ctgggtcacg ccatgtatt ctgccaagga tatcgtgtac attggcttac | 600 |
| gtgacgtcga cccaggtgag cactacatct aaagaccct gggtatcaag tatttcagca | 660 |
| tgacggaagt ggaccgctta ggcatcggca aggtgatgga ggagacgctg agctatctgc | 720 |
| tgggccgtaa gaaacgtcca atccatctga gcttcgatgt tgacggctta gacccgagct | 780 |
| ttacgccagc caccggcacg ccggtcgttg gtggtttaac gtatcgcgaa ggcctgtata | 840 |
| tcacggagga aatctataag acgggtttac tgagcggtct ggacattatg gaggttaatc | 900 |
| caagcttagg taagacgccg gaagaagtta cccgtaccgt taacacggcg gtcgcgatca | 960 |
| cgttagcatg tttcggttta gcccgcgagg gcaaccataa accaattgat tatctgaatc | 1020 |
| caccgaagtg aggatccgaa ttcg | 1044 |

<210> SEQ ID NO 2
<211> LENGTH: 1080
<212> TYPE: DNA
<213> ORGANISM: Artificial Sequence
<220> FEATURE:
<223> OTHER INFORMATION: Synthetic sequence

<400> SEQUENCE: 2

| | |
|---|---|
| gatataccat gggcagcagc catcatcacc accatcacag ctctggtgaa aacttatact | 60 |
| tccaaagcgt ccatagcgtc gcagtgattg gtgccccgtt tagccaaggt caaaaacgca | 120 |
| agggtgttga acatggtccg gcagcgatcc gcgaagcagg tttaatgaag cgtttaagca | 180 |
| gcttaggctg tcacttaaag gatttcggtg atttaagctt tacgccggtc ccaaaggatg | 240 |
| atttatacaa taatctgatc gttaacccac gctctgtggg tctggcgaac caggagctgg | 300 |
| cggaggtcgt gtctcgtgca gtcagcgacg gttatagctg cgttacgctg ggcggtgatc | 360 |
| atagcttagc cattggtacg atttctggtc atgcccgcca ttgcccggat ctgtgtgttg | 420 |
| tgtgggttga tgcgcacgcg gatatcaata cgccactgac cacgtctagc ggtaatttac | 480 |
| acggccagcc ggttagcttc ttattacgtg agctgcaaga caaggtcccg cagttaccag | 540 |
| gcttctcttg gatcaaacca tgtatcagca gcgcatctat tgtctacatt ggcctgcgtg | 600 |
| atgtcgaccc accggagcac ttcatcctga agaattatga catccagtat ttcagcatgc | 660 |
| gtgacatcga ccgtctgggt atccaaaaag ttatggagcg cacgttcgat ctgttaatcg | 720 |
| gcaagcgcca gcgtccgatt cacctgagct ttgacattga cgcctttgac ccgaccctgg | 780 |
| ccccagcaac gggcacgcca gtggttgtg gtttaaccta ccgtgagggt atgtatattg | 840 |
| cagaagagat ccataatacc ggcctgttat ctgccctgga tctggttgaa gtcaatccgc | 900 |
| agctggcaac ctctgaggag gaagcgaaga cgaccgccaa cctggcggtg gacgtcatcg | 960 |
| cctcttcttt cggccagacg cgtgaaggtg gccatatcgt gtatgaccaa ttaccaacgc | 1020 | catctagccc ggacgaatct gagaaccaag cacgtgtccg tatttgagga tccgaattcg    1080

<210> SEQ ID NO 3
<211> LENGTH: 322
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is either methionine or not present

<400> SEQUENCE: 3

Xaa Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu Lys Leu Lys Glu Gln Glu Cys Asp Val Lys
        35                  40                  45

Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
                85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
    130                 135                 140

Val Ser Phe Leu Leu Lys Glu Leu Lys Gly Lys Ile Pro Asp Val Pro
145                 150                 155                 160

Gly Phe Ser Trp Val Thr Pro Cys Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205

Gly Lys Val Met Glu Glu Thr Leu Ser Tyr Leu Leu Gly Arg Lys Lys
    210                 215                 220

Arg Pro Ile His Leu Ser Phe Asp Val Asp Gly Leu Asp Pro Ser Phe
225                 230                 235                 240

Thr Pro Ala Thr Gly Thr Pro Val Val Gly Gly Leu Thr Tyr Arg Glu
                245                 250                 255

Gly Leu Tyr Ile Thr Glu Glu Ile Tyr Lys Thr Gly Leu Leu Ser Gly
            260                 265                 270

Leu Asp Ile Met Glu Val Asn Pro Ser Leu Gly Lys Thr Pro Glu Glu
        275                 280                 285

Val Thr Arg Thr Val Asn Thr Ala Val Ala Ile Thr Leu Ala Cys Phe
    290                 295                 300

Gly Leu Ala Arg Glu Gly Asn His Lys Pro Ile Asp Tyr Leu Asn Pro
305                 310                 315                 320

Pro Lys

<210> SEQ ID NO 4
<211> LENGTH: 333

-continued

```
<212> TYPE: PRT
<213> ORGANISM: Homo sapiens

<400> SEQUENCE: 4

Ser Val His Ser Val Ala Val Ile Gly Ala Pro Phe Ser Gln Gly Gln
1               5                   10                  15

Lys Arg Lys Gly Val Glu His Gly Pro Ala Ala Ile Arg Glu Ala Gly
            20                  25                  30

Leu Met Lys Arg Leu Ser Ser Leu Gly Cys His Leu Lys Asp Phe Gly
        35                  40                  45

Asp Leu Ser Phe Thr Pro Val Pro Lys Asp Asp Tyr Asn Asn Leu
    50                  55                  60

Ile Val Asn Pro Arg Ser Val Gly Leu Ala Asn Gln Glu Leu Ala Glu
65                  70                  75                  80

Val Val Ser Arg Ala Val Ser Asp Gly Tyr Ser Cys Val Thr Leu Gly
                85                  90                  95

Gly Asp His Ser Leu Ala Ile Gly Thr Ile Ser Gly His Ala Arg His
            100                 105                 110

Cys Pro Asp Leu Cys Val Val Trp Val Asp Ala His Ala Asp Ile Asn
        115                 120                 125

Thr Pro Leu Thr Thr Ser Ser Gly Asn Leu His Gly Gln Pro Val Ser
    130                 135                 140

Phe Leu Leu Arg Glu Leu Gln Asp Lys Val Pro Gln Leu Pro Gly Phe
145                 150                 155                 160

Ser Trp Ile Lys Pro Cys Ile Ser Ser Ala Ser Ile Val Tyr Ile Gly
                165                 170                 175

Leu Arg Asp Val Asp Pro Pro Glu His Phe Ile Leu Lys Asn Tyr Asp
            180                 185                 190

Ile Gln Tyr Phe Ser Met Arg Asp Ile Asp Arg Leu Gly Ile Gln Lys
        195                 200                 205

Val Met Glu Arg Thr Phe Asp Leu Leu Ile Gly Lys Arg Gln Arg Pro
210                 215                 220

Ile His Leu Ser Phe Asp Ile Asp Ala Phe Asp Pro Thr Leu Ala Pro
225                 230                 235                 240

Ala Thr Gly Thr Pro Val Val Gly Gly Leu Thr Tyr Arg Glu Gly Met
                245                 250                 255

Tyr Ile Ala Glu Glu Ile His Asn Thr Gly Leu Leu Ser Ala Leu Asp
            260                 265                 270

Leu Val Glu Val Asn Pro Gln Leu Ala Thr Ser Glu Glu Ala Lys
        275                 280                 285

Thr Thr Ala Asn Leu Ala Val Asp Val Ile Ala Ser Ser Phe Gly Gln
    290                 295                 300

Thr Arg Glu Gly Gly His Ile Val Tyr Asp Gln Leu Pro Thr Pro Ser
305                 310                 315                 320

Ser Pro Asp Glu Ser Glu Asn Gln Ala Arg Val Arg Ile
                325                 330
```

ARGININE DEPLETION THERAPY FOR TREATMENT OF GAMT DEFICIENCY

CROSS-REFERENCE TO RELATED APPLICATIONS

This application is the National Stage entry of PCT/US2019/057027, filed on Oct. 18, 2019, which claims priority to United States Provisional Application. Ser. No. 62/747,837, filed Oct. 19, 2018, the entire disclosures of which are hereby incorporated by reference herein.

SEQUENCE LISTING

A sequence list entitled 218107_0013_00_WO_594073_ST25.txt having 9,110 bytes and a date of Oct. 18, 2019 is submitted with the specification and is incorporated into the specification.

BACKGROUND

Guanidinoacetate methyltransferase (GAMT) deficiency (MIM 601240) is an autosomal recessive inborn error of creatine synthesis, biochemically reflecting creatine deficiency and a marked accumulation of guanidinoacetate (GAA) in brain and body fluids, which results in a number of physical or mental disabilities, such as global developmental delay/intellectual disability (DD/ID) epilepsy, movement disorders, speech or language delay, and behavioral problems. Affected individuals exhibit marked impairment of expressive speech, autistic features, and varying neurological manifestations, including epilepsy and movement disorders (Stockler-Ipsiroglu, S. et al *Molecular Genetics and Metabolism* 111 (2014) 16-25; Dhar S U et al., *Mol. Genet. Metab.*, 2009). Currently recommended treatment is based on the following:
   (a) Oral supplementation of creatine (administered as creatine monohydrate) is used to increase cerebral creatine levels. In addition to increasing creatine/phosphocreatine (Cr/PCr) in the brain, oral creatine supplementation can decrease GAA in body fluids and brain but GAA levels remain markedly elevated in most patients. Even after several months of treatment and despite pharmacological doses of creatine supplementation (0.35-2.0 g/kg/day), Cr/PCr concentrations in the patients' brains remain significantly below the normal range. Besides Cr replenishment, Cr treatment leads to a decreased GAA formation due to the inhibition of the AGAT enzyme by Cr. By solely supplementing Cr an approx. 50% reduction of GAA in body fluids can be achieved. Based on published data on Cr/PCr replenishment in brain after Cr treatment, a preliminary comparison of the slope of brain Cr replenishment by the same dose of Cr between GAMT-D and AGAT-D patients revealed a faster rise and a more complete replenishment of Cr/PCr in the latter group. In contrast to GAMTD, GAA is not increased in AGAT-D. (Schultze, Research Gate, March 2005).
   (b) Strategies to reduce guanidinoacetate (GAA) levels include substrate deprivation via an arginine restricted diet as well as competitive inhibition of arginine glycine amidinotransferase (AGAT) activity via high-dose L-ornithine supplementation. AGAT is the enzyme responsible for GAA synthesis.
   (c) The competitive inhibition and substrate deprivation approach to reduce levels of GAA in affected patients which is believed to be neurotoxic, includes the use of orally administered L-Ornithine (L-ornithine aspartate or L-ornithine hydrochloride) and a medical diet aiming to reduce arginine intake.

Although medical diets aiming to reduce arginine intake and lower systemic arginine availability have been shown to be effective in lowering GAA levels and ameliorating disease manifestations associated with high GAA levels, the required diets are problematic for a number of reasons. Such diets are difficult to comply with as they require protein restriction and the goals over time often need to be changed based on each person's nutritional needs and age requirements; calculating and tracking protein intake can be a difficult and troublesome task for those with protein and arginine restricted diets; the diets often have palatability and taste issues which impact patient quality of life and compliance; and the impact of dietary restriction is limited as a high proportion of systemic arginine is the result of tissue turnover and therefore not impacted by dietary restriction. (Crombez, E A, and Cederbaum, S D, *Mol. Genet. Metab.* 2005; Burrage, L. C., et al., *Hum. Mol. Genet.* 2015; Carvalho, D. R., et al., *Ped. Neurol.* 2012; Stockler-Ipsiroglu, S. et al., 2014; Viau, K. S. et al., *Mol. Genet. Metab.* 2013; Mercimek-Mahmutoglu, S. et al., *Gene,* 2015).

SUMMARY

Provided here are compounds, compositions and methods for administering an arginine depleting enzyme to treat a deficiency in guanidinoacetate methyltransferase (GAMT) activity or to treat guanidinoacetate (GAA) toxicity in a subject. The compounds and compositions can reduces arginine levels in the subject and at the same time provides ornithine from the arginase mediated metabolism of arginine.

Thus, a method of treating a deficiency in guanidinoacetate methyltransferase (GAMT) activity in a subject, comprising administering to said subject a pharmaceutical composition comprising a therapeutic amount of an arginine depleting enzyme. The arginine depleting enzyme can be a mammalian or a bacterial arginase enzyme. The arginine depleting enzyme can be a human arginine depleting enzyme. The arginine depleting enzyme can be a human arginase enzyme, a human arginine deiminase enzyme or a combination of these enzymes. The enzymes contemplated can also include enzyme variants of the human arginase enzyme or human arginine deiminase enzyme, wherein the enzyme variant is modified by a substitution, a deletion, an insertion, or a truncation, or a combination thereof in the amino acid sequence of the enzyme. The human arginase enzyme can be a human Arginase I enzyme or a human Arginase II enzyme. The human arginase enzyme can be Arginase 1 (SEQ ID NO: 3) with a metal cofactor of $Co^{+2}$ that is pegylated and lacks the amino terminal methionine; additionally it can be Arginase 1 with one or more substitutions or mutations in the polypeptide sequence.

The method of treatment/use described herein also contemplates human, bacterial or mammalian Arginase I enzyme is engineered with a substituted non-native metal cofactor comprising cobalt.

The methods described can use employ an autologous red blood cell ghost for administering an arginine depleting enzyme.

The method of treatment for deficiency in GAMT activity is associated with a genetic deficiency in a gene encoding a guanidinoacetate methyltransferase enzyme in a subject.

The enzymes for use in these methods, such as a human arginase enzyme or a human arginine deiminase enzyme can be stabilized by association with a stabilizing agent. Stabilizing agents is selected from the group consisting of: a polyethylene glycol (PEG), a synthetic protein polymer, a polysialic acid, an Fc fusion, and albumin. The human arginase enzyme or human arginine deiminase enzyme can further be pegylated. The PEG can be from 1 kD to 10 kD in size, and any integer in between. The human arginase enzyme for use in the methods and compositions can be a pegylated human Arginase I enzyme.

The methods of treatment or use of a medicament can be for a mammal, for example a human.

Another aspect contemplates a method of treatment of a deficiency in guanidinoacetate methyltransferase (GAMT) activity or to treat guanidinoacetate (GAA) toxicity in a subject using a compound or composition having a human Arginase I enzyme having a $k_{cat}/K_M$ for the hydrolysis of arginine of between 400 mM$^{-1}$ s$^{-1}$ and 4,000 mM$^{-1}$ s$^{-1}$ at pH 7.4 and 37° C. when measured in vitro. It is also contemplated that the human Arginase I enzyme and Arginase 1 enzyme can comprise a ratio of cobalt to arginase I enzyme of from 2 µg Co/mg arginase to 3 µg Co/mg arginase. The Arginase I enzyme and Arginase 1 enzyme can be produced by contacting the apoenzyme form with cobalt or a cobalt ion at a temperature of 30° C. to 55° C. for 15 minutes to 60 minutes.

Also contemplated is a method of treating effects of guanidinoacetate (GAA) toxicity in a subject with a deficiency in guanidinoacetate methyltransferase (GAMT) activity, comprising administering to said subject a therapeutic amount of a pharmaceutical composition comprising a pegylated human Arginase I enzyme comprising a cobalt cofactor. The therapeutic amount of the pharmaceutical composition can continue for a period until the subject exhibits an improvement in a physical or neurological condition. The types of physical or neurological conditions contemplated can include conditions selected from the group consisting of: a global developmental delay/intellectual disability (DD/ID), epilepsy, a movement disorder, a speech or language delay, and a behavioral disorder. The method contemplates a therapeutic amount of the pegylated human Arginase I or II enzyme (e.g., a pegylated arginase 1 enzyme such as AEB1102) that can comprise a cobalt cofactor is from about 0.01 mg/kg to about 7.5 mg/kg, from about 0.05 mg/kg to about 5 mg/kg, or from about 0.1 mg/kg to about 5 mg/kg. The therapeutic amount of the composition can be administered topically, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, subcutaneously, subconjunctival, intravesicularlly, mucosally, intrapericardially, intraumbilically, orally, by inhalation, by injection, by infusion, by continuous infusion, by localized perfusion bathing target cells directly, via a catheter, or via a lavage. In one aspect, the method contemplates administration of the pharmaceutical composition being adapted for subcutaneous administration to the subject. For a subcutaneous formulation, an exemplary pharmaceutical composition can comprise a therapeutic dose of an arginase in potassium phosphate, NaCl, sucrose, and PS80 at pH 6.7. For intravenous administration, an exemplary pharmaceutical composition can comprise a pegylated human Arginase I or II enzyme, saline, and glycerol at pH 7.4. The method contemplates administering a pharmaceutical composition sufficient to reduce the serum arginine content in the subject by at least 50% to 99%, or by 90% to 99%, or by 90% to 99%. The method contemplates administering the pharmaceutical composition that can be sufficient to reduce the serum arginine content in the subject by 50% to 99%, or by 90% to 99%, or by 90% to 99%. The method also contemplates administering the pharmaceutical composition in an amount sufficient to reduce the serum GAA level in the patient by at least 25%, at least 30%, at least 35%, at least 40%, at least 50%, or more to the extent GAA levels can be depleted. The method can use a concentration of the pharmaceutical composition in plasma reaches a maximum level 20 to 28 hours after a single administration or reaches a maximum level about 24 hours after a single administration.

Another method contemplated includes a method of treating effects of guanidinoacetate (GAA) toxicity, comprising administering to a subject in need thereof, a therapeutic amount of a pharmaceutical composition comprising an arginine depleting enzyme. The arginine depleting enzyme can be an arginase or arginine deiminase enzyme. A method of treating a deficiency in guanidinoacetate methyltransferase (GAMT) activity in a subject, is also contemplated that comprises the steps of administering to said subject a pharmaceutical composition comprising a therapeutic amount of an arginine depleting enzyme in combination with ornithine supplementation. The method contemplates using an arginine depleting enzyme that can be an arginase or arginine deiminase enzyme. The method also contemplates a pharmaceutical composition that further supplements a high-dose of L-ornithine. The L-ornithine in the pharmaceutical composition of the method can be administered orally as L-ornithine aspartate or L-ornithine hydrochloride.

Also contemplates is a pharmaceutical composition comprising a therapeutic amount of an arginine depleting enzyme for use as a medicament for use in the treatment of a deficiency in guanidinoacetate methyltransferase (GAMT) activity in a subject or treating effects of guanidinoacetate (GAA) toxicity in a subject.

Also contemplated is a pharmaceutical composition comprising a therapeutic amount of an arginine depleting enzyme for use in the treatment of a deficiency in guanidinoacetate methyltransferase (GAMT) activity in a subject or treating effects of guanidinoacetate (GAA) toxicity in a subject.

BRIEF DESCRIPTION OF THE FIGURES

The following drawings form part of the present specification and are included to further demonstrate certain aspects of the compositions and methods of use of the compositions.

DESCRIPTION

Figure 1:
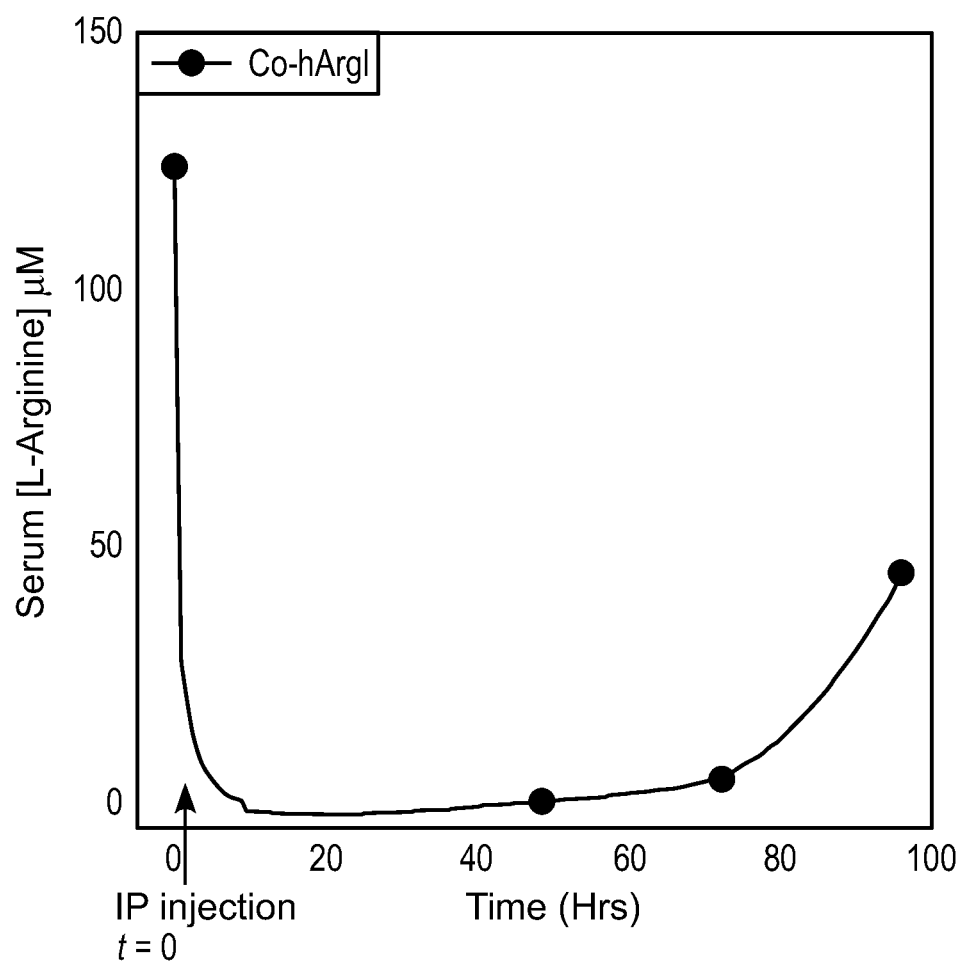
FIG. 1 is a graph showing serum L-arginine depletion in the mouse model. Serum L-Arg concentrations of Balb/c mice treated with a single IP dose of Co-hArgI are kept ≤ to 3-4 µM for over 3 days.

Described herein is an arginase therapy for arginine depletion and GAA reduction or depletion. The disclosed methods offer certain advantages over the current state of the art, including at least higher effectiveness for substrate deprivation, substantially greater impact on systemic arginine levels, and better reduction or depletion of GAA levels. In addition, the approach offers a number of advantages for patients given the adverse impact of dietary restriction of arginine on patients' quality of life and health.

The disclosed methods represent a paradigm shift in how to approach substrate reduction for patients with GAMT. In addition to being more effective in reducing availability of arginine as a substrate it has the potential to allow GAMT deficient patients to suppress GAA production with a reduced requirement for dietary arginine restriction. The disclosed methods thus improve the quality of life by removing difficulties in pursuing activities that are adversely impacted by the complexity and unpleasantness of a medical diet.

Provided are compositions and methods for the treatment of GAMT deficiency and/or GAA toxicity with enzymes that deplete L-arginine in serum, i.e., arginine depleting enzymes. Also contemplated is an use of arginase enzymes and variants thereof wherein the native metal cofactor ($Mn^{2+}$) is replaced with another metal. An exemplary arginase enzyme comprises an amino acid sequence of human Arginase I or an amino acid sequence of human Arginase II and a non-native metal cofactor. Nucleotide sequences of human Arginase I and human Arginase II (SEQ ID NOs: 1 and 2, respectively) and amino acid sequences of human Arginase I and human Arginase II (SEQ ID NOs: 3 and 4, respectively) are provided below ("X" can be methionine or nothing):

(SEQ ID NO: 1)
GATATACCATGGGTTCTTCTCACCATCATCACCACCACAGCTCTGGCGA

GAACCTGTACTTCCAGTCTGCGAAGAGCCGTACGATCGGCATTATTGGT

GCGCCGTTCTCTAAAGGTCAGCCACGCGGTGGTGTGGAAGAGGGTCCGA

CGGTTCTGCGTAAGGCCGGTTTATTAGAAAAGCTGAAAGAGCAGGAGTG

CGACGTTAAGGACTACGGTGACTTACCATTCGCGGACATCCCGAATGAT

AGCCCGTTCCAAATCGTTAAGAATCCGCGCTCTGTGGGTAAAGCAAGCG

AGCAGTTAGCAGGTAAGGTGGCCGAGGTCAAGAAAAACGGTCGTATTAG

CCTGGTTTTAGGCGGTGATCATAGCTTAGCAATTGGCTCTATCTCTGGT

CATGCCCGTGTGCACCCAGATTTAGGTGTCATTTGGGTTGACGCCCATA

CGGATATCAATACGCCATTAACGACCACCAGCGGCAATCTGCATGGCCA

GCCGGTTAGCTTCTTACTGAAGGAGCTGAAGGGTAAAATTCCAGATGTT

CCGGGCTTTAGCTGGGTCACGCCATGTATTTCTGCCAAGGATATCGTGT

ACATTGGCTTACGTGACGTCGACCCAGGTGAGCACTACATCTTAAAGAC

CCTGGGTATCAAGTATTTCAGCATGACGGAAGTGGACCGCTTAGGCATC

GGCAAGGTGATGGAGGAGACGCTGAGCTATCTGCTGGGCCGTAAGAAAC

GTCCAATCCATCTGAGCTTCGATGTTGACGGCTTAGACCCGAGCTTTAC

GCCAGCCACCGGCACGCCGGTCGTTGGTGGTTTAACGTATCGCGAAGGC

CTGTATATCACGGAGGAAATCTATAAGACGGGTTTACTGAGCGGTCTGG

ACATTATGGAGGTTAATCCAAGCTTAGGTAAGACGCCGGAAGAAGTTAC

CCGTACCGTTAACACGGCGGTCGCGATCACGTTAGCATGTTTCGGTTTA

GCCCGCGAGGGCAACCATAAACCAATTGATTATCTGAATCCACCGAAGT

GAGGATCCGAATTCG (SEQ ID NO: 2)
GATATACCATGGGCAGCAGCCATCATCACCACCATCACAGCTCTGGTGA

AAACTTATACTTCCAAAGCGTCCATAGCGTCGCAGTGATTGGTGCCCCG

TTTAGCCAAGGTCAAAAACGCAAGGGTGTTGAACATGGTCCGGCAGCGA

TCCGCGAAGCAGGTTTAATGAAGCGTTTAAGCAGCTTAGGCTGTCACTT

AAAGGATTTCGGTGATTTAAGCTTTACGCCGGTCCCAAAGGATGATTTA

TACAATAATCTGATCGTTAACCCACGCTCTGTGGGTCTGGCGAACCAGG

AGCTGGCGGAGGTCGTGTCTCGTGCAGTCAGCGACGGTTATAGCTGCGT

TACGCTGGGCGGTGATCATAGCTTAGCCATTGGTACGATTTCTGGTCAT

GCCCGCCATTGCCCGGATCTGTGTGTTGTGTGGGTTGATGCGCACGCGG

ATATCAATACGCCACTGACCACGTCTAGCGGTAATTTACACGGCCAGCC

GGTTAGCTTCTTATTACGTGAGCTGCAAGACAAGGTCCCGCAGTTACCA

GGCTTCTCTTGGATCAAACCATGTATCAGCAGCGCATCTATTGTCTACA

TTGGCCTGCGTGATGTCGACCCACCGGAGCACTTCATCCTGAAGAATTA

TGACATCCAGTATTTCAGCATGCGTGACATCGACCGTCTGGGTATCCAA

AAAGTTATGGAGCGCACGTTCGATCTGTTAATCGGCAAGCGCCAGCGTC

CGATTCACCTGAGCTTTGACATTGACGCCTTTGACCCGACCCTGGCCCC

AGCAACGGGCACGCCAGTGGTTGGTGGTTTAACCTACCGTGAGGGTATG

TATATTGCAGAAGAGATCCATAATACCGGCCTGTTATCTGCCCTGGATC

TGGTTGAAGTCAATCCGCAGCTGGCAACCTCTGAGGAGGAAGCGAAGAC

GACCGCCAACCTGGCGGTGGACGTCATCGCCTCTTCTTTCGGCCAGACG

CGTGAAGGTGGCCATATCGTGTATGACCAATTACCAACGCCATCTAGCC

CGGACGAATCTGAGAACCAAGCACGTGTCCGTATTTGAGGATCCGAATT

CG (Human Arginase I)
(SEQ ID NO: 3)
XSAKSRTIGIIGAPFSKGQPRGGVEEGPTVLRKAGLLEKLKEQECDVKD

YGDLPFADIPNDSPFQIVKNPRSVGKASEQLAGKVAEVKKNGRISLVLG

GDHSLAIGSISGHARVHPDLGVIWVDAHTDINTPLTTTSGNLHGQPVSF

LLKELKGKIPDVPGFSWVTPCISAKDIVYIGLRDVDPGEHYILKTLGIK

YFSMTEVDRLGIGKVMEETLSYLLGRKKRPIHLSFDVDGLDPSFTPATG

TPVVGGLTYREGLYITEEIYKTGLLSGLDIMEVNPSLGKTPEEVTRTVN

TAVAITLACFGLAREGNHKPIDYLNPPK

-continued (human arginase II)

(SEQ ID NO: 4)
SVHSVAVIGAPFSQGQKRKGVEHGPAAIREAGLMKRLSSLGCHLKDFGD

LSFTPVPKDDLYNNLIVNPRSVGLANQELAEVVSRAVSDGYSCVTLGGD

HSLAIGTISGHARHCPDLCVVWVDAHADINTPLTTSSGNLHGQPVSFLL

RELQDKVPQLPGFSWIKPCISSASIVYIGLRDVDPPEHFILKNYDIQYF

SMRDIDRLGIQKVMERTFDLLIGKRQRPIHLSFDIDAFDPTLAPATGTP

VVGGLTYREGMYIAEEIHNTGLLSALDLVEVNPQLATSEEEAKTTANLA

VDVIASSFGQTREGGHIVYDQLPTPSSPDESENQARVRI

In some embodiments, the non-native metal is cobalt (Co'). Human Arginase I and II proteins have two Mn (II) sites as their native metal co-factor; either or both Mn sites can be substituted with a non-native metal co-factor so as to generate a modified Arginase I or II protein with a non-native metal cofactor. Therefore, as used herein, "a non-native metal cofactor" is a metal other than manganese. The protein can display a $k_{cat}/K_M$ greater than 400 mM$^{-1}$ s$^{-1}$ at pH 7.4. An exemplary arginase enzyme can display a $k_{cat}/K_M$ between 400 mM$^{-1}$ s$^{-1}$ and 4,000 mM$^{-1}$ s$^{-1}$ at pH 7.4. Another exemplary arginase enzyme can display a $k_{cat}/K_M$ between 400 mM$^{-1}$ s$^{-1}$ and 2,500 mM$^{-1}$ s$^{-1}$ at pH 7.4 at 37° C. Also contemplated is a arginase enzyme comprising an amino acid sequence of human Arginase I or II and a non-native metal cofactor, wherein said protein exhibits a $k_{cat}/K_M$ greater than 400 mM$^{-1}$ s$^{-1}$ at 37° C., pH 7.4.

In certain embodiments, the human Arginase I or II enzyme or other arginine depleting enzyme is stabilized by association with a stabilizing agent in order to increase the half-life of the enzyme in the serum of a patient. As used herein "association" can include any of a number of types of association including, but not limited to covalent or non-covalent bonds, and can also include a protein fusion expressed from an engineered nucleic acid construct, from a hydrogen bonding or hydrophobic interaction and others known to those of skill in the art.

Stabilizing agents for use in the disclosed methods can include but are not limited to polyethylene glycol (PEG), often referred to as pegylation, including various pegylation polymers and linkers, including but not limited to the TransCon linker technology marketed by Ascendis Pharma, conjugation to one or more homogenous synthetic protein polymers, referred to as extenylation and commercially available under the trade name Xten®, polysialylation marketed as PSAylation or Polyxen, by Xenetic Biosciences, PASylation®, marketed by XL-Protein GmbH conjugation to one or more Fc fragments or to a serum protein like albumin, for example. See e.g., U.S. Pat. Nos. 8,679,479 and 9,050.340, incorporated by reference herein. A preferred range of arginase pegylation is 1,000 to 10,000 Daltons and any range in-between, e.g., 5,000 Daltons.

Arginine depleting enzymes useful in the practice of the methods can include arginase enzymes, arginine deiminase enzymes or a combination thereof. The enzymes can be mammalian enzymes such as human or primate enzymes, recombinant human enzymes, engineered human enzymes or enzymes from other species, either mammalian or bacterial, for example, including but not limited to mycoplasma. Non-human arginine depleting enzymes can be delivered by autologous red blood cell ghosts, for example. Red blood cell ghosts are also referred to as engineered red blood cells or red blood cell microparticles (RBC MPs). See e.g., Villa, C. H., et al., (2016) and U.S. Pat. No. 10,004,764 to the University of Pittsburgh regarding the use of such particles as delivery agents for the enzymes discussed herein.

A native (wild-type) arginine depleting enzyme, such as an arginase can be modified by the substitution of the metal cofactor. An arginase enzyme can be modified by substitution of the metal cofactor in addition to other modifications, such as substitutions, deletions, insertions, truncations, or stabilization by conjugation to a stabilizing protein or polymer, such as by pegylation. An exemplary arginine depleting enzyme can comprise a native (wild-type) amino acid sequence of human (or primate) Arginase I or II and a non-native metal cofactor; the amino acid sequence can also lack part of the native sequence. The non-native metal cofactor for an arginase can be cobalt.

The arginase for use as an active agent in the contemplated compositions can lack a portion of the wild-type sequence. For example, the amino acid sequence can be a truncated Arginase I or Arginase II sequence. In another example, the arginase can be Arginase II lacking the first 21 amino acids of the wild-type sequence. Another arginase (wild-type or an engineered variant) for use in the disclosed compositions can lack an N-terminal methionine (e.g., SEQ ID NO: 3).

In another aspect, an arginine depleting enzyme, such as an arginase enzyme or arginine deiminase enzyme, can comprise at least one amino acid substitution. For exemplary arginase enzymes, the enzyme displays an increased catalytic activity under physiological conditions and especially at the pH of human serum (pH 7.4) when compared with native (wild-type) human Arginase I or II protein. In some embodiments, the arginase enzyme or variant is a human Arginase I protein or human Arginase II protein, such as those described in U.S. Pat. No. 9,050,340 incorporated herein by reference. The arginase enzyme can comprises one, two, three, four, five, six, seven, eight, nine, or ten amino acid insertions, deletions or substitutions in the arginase polypeptide sequence. A contemplated arginase enzyme can also have the amino terminus truncated, or the amino terminal methionine removed (e.g., SEQ ID NO: 3), or a combination of these mutations. Another exemplary arginase further comprises a non-native metal cofactor. In particular embodiments, the non-native metal cofactor is $Co^{+2}$. Substitution of the $Mn^{+2}$ cofactor with $Co^{+2}$ results in marked increase in catalytic activity and a drastic reduction in $K_M$ at physiological pH.

Fusion proteins are also contemplated for use with the arginine depleting enzymes; the fusion proteins can comprise an arginine depleting enzyme and a non-arginine depleting enzyme. The non-arginine depleting enzyme sequence can comprise, for example, at least a portion of the Fc region of an immunoglobulin, e.g., to increase the half-life of the arginase in serum when administered to a patient. The Fc region or portion thereof may be any suitable Fc region. In certain embodiments, the Fc region or portion thereof is an IgG Fc region. The amino acid sequence having arginase depleting activity is selected from the group consisting of: a native or mutated arginine deiminiase enzyme, a native or mutated amino acid sequence of human Arginase I (e.g., Arginine 1) and a native or mutated amino acid sequence of human Arginase II enzyme or other arginine depleting enzymes known in the art. In certain embodiments, a dimeric Fc-arginase fusion protein, albumin, or a synthetic protein conjugation is contemplated.

The arginine depleting enzyme in the fusion protein may be native, mutated, and/or otherwise modified, e.g., metal cofactor modified arginase enzyme. The arginine depleting enzyme may contain deletions, substitutions, truncations or a combination thereof. One example contemplates an Fc-arginase containing fusion protein, wherein the arginase is an Arginase I. In further embodiments, the arginine depleting enzyme lacks a portion of the wild-type sequence. The arginine depleting enzyme can be Arginase I lacking an N-terminal methionine or Arginase II, wherein the Arginase II lacks the first 21 amino acids of the wild-type Arginase II sequence. Alternatively, the arginase enzyme may comprise a non-native metal cofactor. In these embodiments, either or both sites can be substituted to generate a fusion protein comprising an amino acid sequence of human Arginase I or II and a non-native metal cofactor. In some embodiments, the non-native metal cofactor is cobalt. In some embodiments, the arginase contains a mutation in the polypeptide sequence in the form of an amino acid substitution, a deletion, an insertion, or a truncation, or a combination thereof. Exemplary arginase enzymes for use in the present disclosure are more fully described in U.S. Pat. No. 8,440,184, incorporated herein in its entirety by reference.

The present disclosure includes a method of treating a human GAMT patient comprising administering a formulation comprising a fusion protein, the fusion protein comprising an amino acid sequence having an arginine depleting enzyme activity and at least a portion of the Fc region of a human immunoglobulin to the patient. Described formulations can comprise an amino acid sequence having human arginase activity higher than that displayed by the native human arginase enzymes or human arginine deiminase enzymes at physiological conditions and further comprising one or more attached polyethylene glycol chain(s). The formulation can be a pharmaceutical formulation comprising any of the above discussed arginine depleting enzymes, e.g., arginase enzymes, and a pharmaceutically acceptable excipients. Such pharmaceutically acceptable excipients are well known to those having skill in the art. All of the described arginine depleting enzymes are contemplated as useful for human therapy.

The formulation may in some circumstances be administered topically, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, subcutaneously, subconjunctival, intravesicularlly, mucosally, intrapericardially, intraumbilically, orally, by inhalation, by injection, by infusion, by continuous infusion, by localized perfusion bathing target cells directly, via a catheter, or via a lavage.

All of the above mentioned arginine depleting enzyme, (e.g., arginases and arginine deiminase enzymes and variant enzymes thereof) are contemplated in a preferred embodiment as purified or isolated proteins, and preferably monomeric proteins.

The term "therapeutically effective" as used herein refers to an amount of an active agent and/or therapeutic or pharmaceutical composition (such as a therapeutic polynucleotide and/or therapeutic polypeptide) that is employed in methods of treating a subject to achieve a therapeutic effect, such as wherein at least one symptom of a condition being treated in the subject is at least ameliorated. Therapeutic effect also can include reduction or depletion of a level of arginine and/or GAA in a subject.

The term "treat" as used herein refers to the administration of medical or other therapy in a subject directed to the improvement, inhibition, prevention, amelioration, reversal, or otherwise beneficial effect of or to a particular condition or disease. The term does not inherently require any particular outcome.

Other objects, features and advantages of the methods and compositions described will become apparent from the following detailed description. It should be understood, however, that the detailed description and the specific examples, while indicating exemplary embodiments, are given by way of illustration only, since various changes and modifications within the spirit and scope of the described compositions and methods will become apparent to those skilled in the art from this detailed description.

Described herein are compositions and methods for the treatment of a deficiency in guanidinoacetate methyltransferase (GAMT) activity or treatment of a GAA toxicity, which can be associated with a genetic deficiency in a gene encoding or affecting the expression of the guanidinoacetate methyltransferase enzyme with enzymes that deplete L-arginine. Both native and mutated or engineered enzymes are contemplated, as well as enzymes with modified metal cofactors, enzymes fused to other polypeptides as well as enzymes conjugated to polymers that increase serum persistence, e.g., high molecular weight polyethylene glycol or polysialic acid, for example.

I. Arginine Depleting Enzymes

Arginine depleting enzymes contemplated herein include arginase enzymes, Arginase I and II, and arginine deiminase enzymes, and variants thereof.

Arginine deiminase is in the enzyme class L-arginine iminohydrolase. Other synonyms include arginine dihydrolase, citrulline iminase, and L-arginine deiminase. Mycobacterium arginine deiminase catalyzes the formation of L-citrulline from L-arginine as disclosed at NCBI Reference Sequence WP_003405169.1. *Homo sapien* arginine deiminase enzymes include peptidyl arginine deiminase 3 (also known as PADS; PDI3, UHS1) and peptidyl arginine deiminase 1 (also referred to as HPAD10, PAD1, PDI, and PDI1).

Arginase is a manganese-containing enzyme. It is the final enzyme of the urea cycle. Arginase is the fifth and final step in the urea cycle, a series of biophysical reactions in mammals during which the body disposes of harmful ammonia. Specifically, arginases convert L-arginine into L-ornithine and urea.

L-arginine is the nitrogen donating substrate for nitric oxide synthase (NOS), producing L-citrulline and NO. Although the $K_M$ of arginase (2-5 mM) has been reported to be much higher than that of NOS for L-arginine (2-20 µM), arginase may also play a role in regulating NOS activity. Under certain conditions Arginase I is Cys-S-nitrosylated, resulting in higher affinity for L-arginine and reduced availability of substrate for NOS.

Arginase is a homo-trimeric enzyme with an α/β fold of a parallel eight-stranded β-sheet surrounded by several helices. The enzyme contains a di-nuclear metal cluster that is integral to generating a hydroxide for nucleophilic attack on the guanidinium carbon of L-arginine. The native metal for an arginase enzyme is $Mn^{2+}$. These $Mn^{2+}$ ions coordinate water, orientating and stabilizing the molecule and allowing water to act as a nucleophile and attack L-arginine, hydrolyzing it into ornithine and urea.

Mammals have two arginase isozymes (EC 3.5.3.1) that catalyze the hydrolysis of L-arginine to urea and L-ornithine. The Arginase I gene is located on chromosome 6 (6q.23), is highly expressed in the cytosol of hepatocytes, and functions in nitrogen removal as the final step of the urea cycle. The Arginase II gene is found on chromosome 14 (14q.24.1). Arginase II is mitochondrially located in tissues such as kidney, brain, and skeletal muscle where it is thought to provide a supply of L-ornithine for proline and polyamine biosynthesis (Lopez et al., 2005).

Arginases have been investigated for nearly 50 years as a method for degrading extracellular L-arginine (Dillon et al., 2002). Some promising clinical results have been achieved by introducing arginase by transhepatic arterial embolization, following which, several patients experienced partial remission of HCC (Cheng et al., 2005). However, since arginase has a high $K_M$ (~2-5 mM) and exhibits very low activity at physiological pH values, high dosing is required for chemotherapeutic purposes in patients (Dillon et al., 2002). While native arginase is cleared from circulation within minutes (Savoca et al., 1984), a single injection of PEG-arginase MW 5,000 in rats was sufficient to achieve near complete arginine depletion for ~3 days (Cheng et al., 2007).

Cheng et al. made the surprising observation that many human HCC cell lines do not express ornithine transcarbamylase (OTC) (in addition to argininosuccinate synthetase, ASS) and thus human HCC cells are susceptible to PEG-arginase (Cheng et al., 2007). In mice implanted with Hep3b hepatocarcinoma cells, weekly administration of PEG-arginase resulted in tumor growth retardation which was accentuated by co-administration of 5-fluorouracil (5-FU). However, the PEG-arginase was used at the very high doses that are impractical for use in human therapy, reflecting the lower physiological activity of that PEG-arginase.

To address these issues a bacterial arginine hydrolyzing enzyme, arginine deiminase or ADI which displays good kinetics and stability has been tested in vitro and clinically. Unfortunately ADI is a bacterial enzyme and therefore ADI induces strong immune responses and adverse effects in most patients. However, for those patients who do not develop significant adverse responses, an impressive percentage exhibit stable disease or remission.

For clinical use, an arginase should be engineered to allow it to persist for long times (e.g., days) in circulation. In the absence of any modification, human arginase has a half-life of only a few minutes in circulation primarily because its size is not sufficiently large to avoid filtration though the kidneys. Unmodified human arginase is very susceptible to deactivation in serum and it is degraded with a half-life of only four hours.

L-arginine is the sole substrate for nitric oxide synthase (NOS), producing L-citrulline and NO. Although the $K_M$ of arginase (2-5 mM) has been reported to be much higher than that of NOS for L-arginine (2-20 µM), arginase may also play a role in regulating NOS activity (Durante et al., 2007). Under certain conditions Arginase I is Cys-S-nitrosylated, resulting in higher affinity for L-arginine and reduced availability of substrate for NOS (Santhanam et al., 2007). Arginase is a homo-trimeric enzyme with an α/β fold of a parallel eight-stranded β-sheet surrounded by several helices. The enzyme contains a di-nuclear metal cluster that is integral to generating a hydroxide for nucleophilic attack on the guanidinium carbon of L-arginine (Cama et al., 2003; Dowling et al., 2008). The native metal for arginase is $Mn^{2+}$; an arginase enzyme with the native metal co-factor ($Mn^{2+}$) exhibits a pH optimum of 9. At physiological pH the enzyme exhibits more than a 10-fold lower $k_{cat}/K_M$ in hydrolyzing L-arginine. The low catalytic activity displayed by the native human arginase with the native $Mn^{2+}$ arginase enzyme presents a problem for human therapy, since it means that impractical doses of the enzyme may have to be used to achieve a therapeutically relevant reduction in L-arginine plasma levels.

In some aspects, native and mutant arginases are contemplated wherein the natural metal cofactor ($Mn^{2+}$) is replaced with another metal. It has been found that substitution of the metal cofactor in human arginase exerts a beneficial effect on the rate of hydrolysis of L-Arginine and stability under physiological conditions when compared to native human arginase with the natural metal cofactor. The substitution of the native metal ($Mn^{2+}$) with other divalent cations can be exploited to shift the pH optimum of the enzyme to a lower values and thus achieve high rates of L-arginine hydrolysis under physiological conditions. Human Arginase I and II proteins have two Mn (II) sites; therefore, either or both sites can be substituted so as to generate a mutated Arginase I or II protein with a non-native metal cofactor. A suitable non-native metal is cobalt.

The non-native metal can be cobalt ($Co^{2+}$) for the arginase enzymes. Incorporation of $Co^{2+}$ in the place of $Mn^{2+}$ in human Arginase I or human Arginase II results in dramatically higher activity at physiological pH. It was found that a human Arginase I enzyme containing $Co^{2+}$ ("Co-hArgI") displayed a 10 fold increase in $k_{cat}/K_M$ in vitro at pH 7.4, which in turn translated into a 15 fold increase in HCC cytotoxicity and a 13-fold increase in melanoma cytotoxicity as compared to the human Arginase I which contains $Mn^{2+}$ ("Mn-hArgI"). It was also found that a pharmacological preparation of Co-hArgI could clear serum L-Arg for over 3 days in mice with a single injection. Furthermore, it was found that a pharmacological preparation of Co-hArgI could shrink HCC tumor xenografts in nude mice, whereas Mn-hArgI (a $Mn^{+2}$ containing human arginase I enzyme) only slowed tumor growth (Ensor et al., 2002). See also U.S. Pat. Nos. 9,050,340 and 8,679,479, which are herein incorporated by reference.

Methods and compositions related to pegylated arginase enzymes and arginine deiminase enzymes, including pegylated human arginase I and II enzymes, are disclosed. Specifically, pegylation of arginase at an engineered cysteine residue (e.g., substituting the third residue of the N-terminal) may be used to produce a homogenous pegylated arginase composition. Methods for isolation of pegylated arginase based on temporary disruption of polymerization are also disclosed.

An exemplary human Arginase I enzyme comprises SEQ ID NO: 3 or and may optionally further comprise one or more of the following the amino acid substitution is at His101, Asp124, His126, Asp128, Asp232, Asp234, Trp122, Asp181, Ser230, His120, Asp143, His145, Asp147, Asp251, Asp253, Trp141, Asp200, Ser249, Cys303, or Glu256. Alternatively, it can be the native Arginase I with one or more of the mutations indicated in this paragraph either with the native metal co-factor or using another metal co-factor, such as cobalt. A number of mutations have been found to increase the catalytic activity and drastically reduce the $K_m$ for L-Arginine under physiological conditions. Optionally, substitution mutations for the Arginase I proteins and variants described herein can be selected from the group consisting of one or more of the following: Asp181Ser, Ser230Cys, Ser230Gly, Cys303Phe, Cys303Ile, Glu256Gln, Asp181Glu, and Ser230Ala. In some aspects, the present invention provides embodiments where two or more mutations are introduced in human arginase I enzyme. The human Arginase I enzyme can comprise at least two amino acid substitutions. The human Arginase I enzyme can have substitutions at Asp181Glu and Ser230Ala. These variants are also contemplated as having or lacking the N-terminal methionine. Arginase 1 for example is human Arginase I having the sequence of SEQ ID NO: 3, wherein the N-terminal methionine is missing and the co-factor is cobalt and pegylated.

Pegylation is the process of covalent attachment of poly (ethylene glycol) polymer chains to another molecule, normally a drug or therapeutic protein. Pegylation is routinely achieved by incubation of a reactive derivative of PEG with the target macromolecule. The covalent attachment of PEG to a drug or therapeutic protein can "mask" the agent from the host's immune system (reduced immunogenicity and antigenicity), increase the hydrodynamic size (size in solution) of the agent which prolongs its circulatory time by reducing renal clearance. Pegylation can also provide water solubility to hydrophobic drugs and proteins.

The first step in pegylation is the suitable functionalization of the PEG polymer at one or both terminals. PEGs that are activated at each terminus with the same reactive moiety are known as "homobifunctional", whereas if the functional groups present are different, then the PEG derivative is referred as "heterobifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, tyrosine. The N-terminal amino group and the C-terminal carboxylic acid can also be used.

The techniques used to form first generation PEG derivatives are generally reacting the PEG polymer with a group that is reactive with hydroxyl groups, typically anhydrides, acid chlorides, chloroformates, and carbonates. In the second generation pegylation chemistry more efficient functional groups such as aldehyde, esters, amides, etc. made available for conjugation.

As applications of pegylation have become more and more advanced and sophisticated, there has been an increase in need for heterobifunctional PEGs for conjugation. These heterobifunctional PEGs can be useful in linking two entities, where a hydrophilic, flexible and biocompatible spacer is needed. Preferred end groups for heterobifunctional PEGs are maleimide, vinyl sulfones, pyridyl disulfide, amine, carboxylic acids and NHS (N-hydroxysuccinimide) esters.

The most common modification agents, or linkers, are based on methoxy PEG (mPEG) molecules. Their activity depends on adding a protein-modifying group to the alcohol end. In some instances polyethylene glycol (PEG diol) is used as the precursor molecule. The diol is subsequently modified at both ends in order to make a hetero- or homo-dimeric PEG-linked molecule (as shown in the example with PEG bis-vinylsulfone).

The arginine depleting enzymes and variants thereof contemplated herein are generally PEGylated at nucleophilic sites such as unprotonated thiols (cysteinyl residues) or amino groups. Examples of cysteinyl-specific modification reagents include PEG maleimide, PEG iodoacetate, PEG thiols, and PEG vinylsulfone. All four are strongly cysteinyl-specific under mild conditions and neutral to slightly alkaline pH, but each has some drawbacks. The amide formed with the maleimides can be somewhat unstable under alkaline conditions so there may be some limitation to formulation options with this linker. The amide linkage formed with iodo PEGs is more stable, but free iodine can modify tyrosine residues under some conditions. PEG thiols form disulfide bonds with protein thiols, but this linkage can also be unstable under alkaline conditions. PEG-vinylsulfone reactivity is relatively slow compared to maleimide and iodo PEG; however, the thioether linkage formed is quite stable. Its slower reaction rate also can make the PEG-vinylsulfone reaction easier to control.

Site-specific pegylation at native cysteinyl residues is seldom carried out, since these residues are usually in the form of disulfide bonds or are required for biological activity. On the other hand, site-directed mutagenesis can be used to incorporate cysteinyl pegylation sites for thiol-specific linkers. The cysteine mutation must be designed such that it is accessible to the pegylation reagent and is still biologically active after pegylation.

Amine-specific modification agents include PEG NHS ester, PEG tresylate, PEG aldehyde, PEG isothiocyanate, and several others. All react under mild conditions and are very specific for amino groups. The PEG NHS ester is probably one of the more reactive agents; however, its high reactivity can make the pegylation reaction difficult to control at large scale. PEG aldehyde forms an imine with the amino group, which is then reduced to a secondary amine with sodium cyanoborohydride. Unlike sodium borohydride, sodium cyanoborohydride will not reduce disulfide bonds. However, this chemical is highly toxic and must be handled cautiously, particularly at lower pH where it becomes volatile.

Due to the multiple lysine residues on most proteins, site-specific pegylation can be a challenge. Fortunately, because these reagents react with unprotonated amino groups, it is possible to direct the pegylation to lower-pK amino groups by performing the reaction at a lower pH. Generally the pK of the α-amino group is 1-2 pH units lower than the epsilon-amino group of lysine residues. By PEGylating the molecule at pH 7 or below, high selectivity for the N-terminus frequently can be attained. However, this may only be feasible if the N-terminal portion of the protein is not required for biological activity. Still, the pharmacokinetic benefits from pegylation can outweigh a significant loss of in vitro bioactivity, resulting in a product with much greater in vivo bioactivity regardless of pegylation chemistry.

There are several parameters to consider when developing a pegylation procedure. Fortunately, there are usually no more than four or five parameters. The "design of experiments" approach to optimization of pegylation conditions can be very useful. For thiol-specific pegylation reactions, parameters to consider include: protein concentration, PEG-to-protein ratio (on a molar basis), temperature, pH, reaction time, and in some instances, the exclusion of oxygen. Oxygen can contribute to intermolecular disulfide formation by the protein, which will reduce the yield of the PEGylated product. The same factors should be considered (with the exception of oxygen) for amine-specific modification except that pH may be even more relevant, particularly when targeting the N-terminal amino group.

For both amine- and thiol-specific modifications, the reaction conditions may affect the stability of the protein. This may limit the temperature, protein concentration, and pH. In addition, the reactivity of the PEG linker should be known before starting the pegylation reaction. For example, if the pegylation agent is only 70% active, the amount of PEG used should ensure that only active PEG molecules are counted in the protein-to-PEG reaction stoichiometry. How to determine PEG reactivity and quality will be described later.

II. Proteins and Peptides

Compositions are provided that comprise at least one protein or peptide, such as stabilized arginase multimers. These polypeptides may be in a fusion protein or conjugated to an agent as described herein.

As used herein, a protein or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide" are used interchangeably herein. The term protein or polypeptide are used interchangeably with enzyme unless otherwise indicated.

In certain embodiments the size of at least one protein or peptide may comprise, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino acid residues.

As used herein, an "amino acid residue" refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moieties. The sequence of residues of the protein or peptide also may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid, including but not limited to those shown on Table 1 below.

TABLE 1

| Abbr. | Amino Acid |
|---|---|
| Aad | 2-Aminoadipic acid |
| Baad | 3-Aminoadipic acid |
| Bala | β-alanine, β-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |

TABLE 1-continued

Modified and Unusual Amino Acids

| Abbr. | Amino Acid |
|---|---|
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| Alle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and may be found at computerized databases known to those of ordinary skill in the art. Such databases include the National Center for Biotechnology Information's Genbank and GenPept databases (available on the world wide web at ncbi.nlm.nih.gov). The coding regions for known genes may be amplified and/or expressed using the techniques disclosed herein or as would be known to those of ordinary skill in the art. Alternatively, various commercial preparations of proteins, polypeptides and peptides are known to those of skill in the art.

III. Nucleic Acids and Vectors

Also contemplated are nucleic acid sequences encoding a fusion protein for the arginine depleting enzymes discussed herein, such as a stabilized multimeric arginase, are disclosed. Depending on which expression system to be used, nucleic acid sequences can be selected based on conventional methods. For example, human Arginase I and II enzymes contain multiple codons that are rarely utilized in E. coli protein synthesis that may interfere with expression, therefore the respective genes or variants thereof may be codon optimized for E. coli expression. Various vectors may be also used to express the protein of interest, such as a fusion multimeric arginase or a cysteine-substituted arginase. Exemplary vectors include, but are not limited, plasmid vectors, viral vectors, transposon or liposome-based vectors.

IV. Host Cells

Host cells, preferably eukaryotic cells, useful in in producing the arginine depleting enzymes and enzyme variants thereof discussed herein are any that may be transformed to allow the expression and secretion of arginase and fusion multimers thereof. The host cells may be bacteria, mammalian cells, yeast, or filamentous fungi. Various bacteria include Escherichia and Bacillus. Yeasts belonging to the genera Saccharomyces, Kluyveromyces, Hansenula, or Pichia would find use as an appropriate host cell. Various species of filamentous fungi may be used as expression hosts including the following genera: Aspergillus, Trichoderma, Neurospora, Penicillium, Cephalosporium, Achlya, Podospora, Endothia, Mucor, Cochliobolus and Pyricularia.

Examples of usable host organisms include bacteria, e.g., Escherichia coli MC1061, derivatives of Bacillus subtilis BRB 1 (Sibakov et al., 1984), *Staphylococcus aureus* SAI123 (Lordanescu, 1975) or *Streptococcus lividans* (Hopwood et al., 1985); yeasts, e.g., *Saccharomyces cerevisiae* AH 22 (Mellor et al., 1983) and *Schizosaccharomyces pombe*; filamentous fungi, e.g., *Aspergillus nidulans, Aspergillus awamori* (Ward, 1989), *Trichoderma reesei* (Penttila et al., 1987; Harkki et al, 1989).

Examples of mammalian host cells include Chinese hamster ovary cells (CHO-K1; ATCC CCL61), rat pituitary cells (GH$_1$; ATCC CCL82), HeLa S3 cells (ATCC CCL2.2), rat hepatoma cells (H-4-II-E; ATCCCRL 1548), SV40-transformed monkey kidney cells (COS-1; ATCC CRL 1650), and murine embryonic cells (NIH-3T3; ATCC CRL 1658). The foregoing examples being illustrative but not limitative of the many possible host organisms known in the art. In principle, all hosts capable of secretion can be used whether prokaryotic or eukaryotic.

Mammalian host cells expressing the arginase and/or their fusion multimers are cultured under conditions typically employed to culture the parental cell line. Generally, cells are cultured in a standard culture medium containing physiological salts and nutrients, such as standard RPMI, MEM, IMEM or DMEM, typically supplemented with 5-10% serum, such as fetal bovine serum. Culture conditions are also standard, e.g., cultures are incubated at 37° C. in stationary or roller cultures until desired levels of the proteins are achieved.

V. Protein Purification

Protein purification techniques are well known to those of skill in the art. These techniques involve, at one level, the homogenization and crude fractionation of the cells, tissue or organ to polypeptide and non-polypeptide fractions. The protein or polypeptide of interest may be further purified using chromatographic and electrophoretic techniques to achieve partial or complete purification (or purification to homogeneity) unless otherwise specified. Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. A particularly efficient method of purifying peptides is fast performance liquid chromatography (FPLC) or even high performance liquid chromatography (HPLC).

A purified protein or peptide having an arginine depleting enzyme or variant thereof as described herein can also refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various techniques suitable for use in protein purification are well known to those of skill in the art. These include, for example, precipitation with ammonium sulphate, PEG, antibodies and the like, or by heat denaturation, followed by: centrifugation; chromatography steps such as ion exchange, gel filtration, reverse phase, hydroxylapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

There is no general requirement that the protein or peptide always be provided in their most purified state. Indeed, it is contemplated that less substantially purified products may have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

In certain embodiments a protein or peptide may be isolated or purified, for example, a stabilized arginase multimeric fusion protein, or an arginase prior or post pegylation. For example, a His tag or an affinity epitope may be comprised in such a arginase variant to facilitate purification. Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand.

Size exclusion chromatography (SEC) is a chromatographic method in which molecules in solution are separated based on their size, or in more technical terms, their hydrodynamic volume. It is usually applied to large molecules or macromolecular complexes such as proteins and industrial polymers. Typically, when an aqueous solution is used to transport the sample through the column, the technique is known as gel filtration chromatography, versus the name gel permeation chromatography which is used when an organic solvent is used as a mobile phase.

The underlying principle of SEC is that particles of different sizes will elute (filter) through a stationary phase at different rates. This results in the separation of a solution of particles based on size. Provided that all the particles are loaded simultaneously or near simultaneously, particles of the same size should elute together. Each size exclusion column has a range of molecular weights that can be separated. The exclusion limit defines the molecular weight at the upper end of this range and is where molecules are too large to be trapped in the stationary phase. The permeation limit defines the molecular weight at the lower end of the range of separation and is where molecules of a small enough size can penetrate into the pores of the stationary phase completely and all molecules below this molecular mass are so small that they elute as a single band.

High-performance liquid chromatography (or High pressure liquid chromatography, HPLC) is a form of column chromatography used frequently in biochemistry and analytical chemistry to separate, identify, and quantify compounds. HPLC utilizes a column that holds chromatographic packing material (stationary phase), a pump that moves the mobile phase(s) through the column, and a detector that shows the retention times of the molecules. Retention time varies depending on the interactions between the stationary phase, the molecules being analyzed, and the solvent(s) used.

VI. Pharmaceutical Compositions

Contemplated are arginine depleting enzymes and variants thereof, e.g., arginine deiminase enzymes and/or arginase enzymes, in a composition that can be administered systemically either intravenously (i.v.), intrathecally, and/or intraperitoneally (i.p.), or subcutaneously. They can be administered alone or in combination with other treatments related to GAA toxicity.

The contemplated compositions can be formulated together with physiologically tolerable liquid, gel or solid carriers, diluents, and excipients. These therapeutic (pharmaceutical) preparations can be administered for clinical use in humans in a manner similar to other therapeutic biologic agents. In general, the dosage required for therapeutic efficacy will vary according to the type of use and mode of administration, as well as the particularized requirements of individual subjects.

Such compositions are typically prepared as liquid solutions or suspensions, as injectables. Suitable diluents and excipients are, for example, water, saline, dextrose, glycerol, and other FDA approved diluents, and combinations thereof. In addition, if desired the compositions may contain minor amounts of auxiliary substances such as wetting or emulsifying agents, stabilizing or pH buffering agents.

Where clinical applications are contemplated, it may be necessary to prepare pharmaceutical compositions—expression vectors, virus stocks, proteins, antibodies and drugs—in a form appropriate for the intended application. Generally, "pharmaceutical compositions" and "pharmaceutical formulations" as discussed herein comprise an effective amount of one or more arginase variants or additional agent dissolved or dispersed in a pharmaceutically acceptable carrier. The phrases "pharmaceutical" or "pharmacologically acceptable" refers to molecular entities and compositions that do not produce an adverse, allergic or other untoward reaction when administered to an animal, such as, for example, a human, as appropriate. The preparation of an pharmaceutical composition that contains at least one arginase enzyme or variant, such as a stabilized multimeric arginase or a pegylated arginase isolated by the method disclosed herein, or additional active ingredient will be known to those of skill in the art in light of the present disclosure, as exemplified by REMINGTON'S PHARMACEUTICAL SCIENCES, 18$^{th}$Ed., 1990, incorporated herein by reference. Moreover, for animal (e.g., human) administration, it will be understood that preparations should meet sterility, pyrogenicity, general safety and purity standards as required by FDA Office of Biological Standards.

As used herein, a "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, REMINGTON'S PHARMACEUTICAL SCIENCES, 18$^{th}$ Ed., 1990, incorporated herein by reference). Except insofar as any conventional carrier is incompatible with the active ingredient, its use in the pharmaceutical compositions is contemplated.

The contemplated arginine deiminase enzymes and arginase enzymes and variants thereof described herein compositions can be formulated with carriers depending on whether it is to be administered in solid, liquid or aerosol form, and whether it need to be sterile for such routes of administration as injection. The pharmaceutical compositions can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in lipid compositions (e.g., liposomes), or by other method or any combination of the forgoing as would be known to one of ordinary skill in the art (see, for example, REMINGTON'S PHARMACEUTICAL SCIENCES, 18$^{th}$ Ed., 1990, incorporated herein by reference).

The arginine depleting enzymes may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

The contemplated compositions suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of treatment and use described.

Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The contemplated compositions can be combined with a carrier in any convenient and practical manner, i.e., by solution, suspension, emulsification, admixture, encapsulation, absorption and the like. Such procedures are routine for those skilled in the art.

The composition can be combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

A pharmaceutical lipid vehicle can be used in compositions that include arginase variants, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods described herein.

One of ordinary skill in the art would be familiar with the range of techniques that can be employed for dispersing a composition in a lipid vehicle. For example, the stabilized multimeric or pegylated arginase may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition, pharmaceutical composition, or active agent described herein that can be administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

For a pharmaceutical composition comprising Arginase 1 (SEQ ID NO: 3, but lacking the N-terminal methionine, having cobalt as the co-factor and pegylated), an exemplary amount for administration to a subject can range from 0.01 mg/kg to 7.5 mg/kg subject weight, or from 0.05 mg/kg to 5.0 mg/kg, or from 0.1 mg/kg to 5.0 mg/kg (and any 0.1 value in between 0.1 mg/kg to 5.0 mg/kg).

Therapeutic effectiveness for improvement of a neuromotor function for the conditions contemplated herein are determined after the initial administration of the arginine and/or GAA reducing agent. The neuromotor function can be one or more of, without limitation, improvement in the stepping by the patient, walking by the patient, reduced spasticity in the patient, and/or increased alertness. Another method contemplates that the subject exhibits at least one of: less resting spasticity, fewer leg cramps related to spasticity, adaptive behavior, and improved PROMIS T-score after initial administration of the arginine depleting enzyme (e.g., arginase and arginine deiminase) compared to at least one of spasticity, behavior, and PROMIS T-score before administration of the arginase. Response to treatment with the arginase such that one or more toxic metabolites (e.g., GAA) are reduced from their initial levels by at least 30%, 40%, 50%, 60%, 70%, 80% etc. to a normal level or cleared.

The method of treating a subject is administered repeated doses of the arginine depleting enzyme composition. After receiving multiple doses, the patient may exhibit improvement in at least one of: (a) mobility or (b) adaptive behavior, relative to a baseline to said mobility or adaptive behavior for the subject before therapy.

Therapeutically effective amounts when administered to a patient can also improve muscle strength, ambulatory ability of a patient (i.e., ability to run, walk, ride a bike, climb stairs without support), and improve cognitive ability (for example Wechsler Intelligence Scale for Children (WISC) testing improvement) and/or adaptive behavior (for example Adaptive Behavior Assessment Scale (ABAS) or Vineland Adaptive Behavior Scale (VABS) testing improvement) (Lopata et al., "Comparison of Adaptive Behavior Measures for Children with HFASDs," *Autism Researc and Treatment*, Vol. 2013, pp. 1-10, (2013)).

VII. Definitions

The term "aa" refers to amino acid(s) Amino acid substitutions are indicated by the amino acid position, e.g. 303, in the molecule using a letter code (the letter in front of the number indicates the amino acid being replaced, while the letter after the number indicates the amino acid being introduced).

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the composition, device or method being employed to determine the value.

Following long-standing patent law, the words "a" and "an," when used in conjunction with the word "comprising" in the claims or specification, denotes one or more, unless specifically noted.

As used herein the term "portion" when in reference to a protein (as in "a portion of a given protein") refers to fragments of that protein. The fragments may range in size from four amino acid residues to the entire amino acid sequence minus one amino acid.

As used herein the terms "protein" and "polypeptide" refer to compounds comprising amino acids joined via peptide bonds and are used interchangeably. The proteins and polypeptides discussed herein can be an arginine depleting enzyme such as arginine deiminase enzyme or an arginase, such as Arginase I or II enzymes or a fusion protein to be fused to an arginine depleting enzyme. The protein can be bacterial or mammalian. Mammalian enzymes can include rodent, human, primate, etc. These proteins can be native proteins or genetically modified recombinant proteins. Exemplary proteins include arginine depleting enzymes that are truncated at their amino or carboxy termini or be otherwise genetically modified variants as described herein.

As used herein, the term "fusion protein" refers to a chimeric protein containing the protein of interest (i.e., a human arginase or variant thereof) joined (or operably linked) to an exogenous protein fragment (the fusion partner which consists of a non-arginase enzyme or a non-arginine deiminase). The fusion partner may enhance serum half-life, solubility, or both. It may also provide an affinity tag (e.g. his-tag) to allow purification of the recombinant fusion protein from the host cell or culture supernatant, or both.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "$K_m$" as used herein refers to the Michaelis-Menten constant for an enzyme and is defined as the concentration of the specific substrate at which a given enzyme yields one-half its maximum velocity in an enzyme catalyzed reaction.

The term $k_{cat}$ as used herein refers to the turnover number or the number of substrate molecule each enzyme site converts to product per unit time, and in which the enzyme is working at maximum efficiency.

The term $K_{cat}/K_m$ as used herein is the specificity constant which is a measure of how efficiently an enzyme converts a substrate into product.

The term "Mn-hArgI" refers to human Arginase I with an Mn (II) cofactor. The term "Co-hArgI" refers to human Arginase I (mutant or native) with a Co (II) cofactor.

The term "$IC_{50}$" is the half maximal (50%) inhibitory concentration (IC) and thus a measure of effectiveness.

The term "pegylated" refers to conjugation with polyethylene glycol (PEG), which has been widely used as a drug carrier, given its high degree of biocompatibility and ease of modification. (Harris et al., 2001). Attachment to various drugs, proteins, and liposomes has been shown to improve residence time and decrease toxicity. (Greenwald et al., 2000; Zalipsky et al., 1997). PEG can be coupled (e.g. covalently linked) to active agents through the hydroxyl groups at the ends of the chain and via other chemical methods; however, PEG itself is limited to at most two active agents per molecule. In a different approach, copolymers of PEG and amino acids have been explored as novel biomaterials which would retain the biocompatibility properties of PEG, but which would have the added advantage of numerous attachment points per molecule (providing greater drug loading), and which can be synthetically designed to suit a variety of applications (Nathan et al., 1992; Nathan et al., 1993). In one aspect, an arginase is pegylated with 1,000 to 10,000 Daltons of polyethylene glycol, e.g., with 5,000 Daltons. See for example U.S. Pat. No. 8,679,479 incorporated herein by reference.

The term "gene" refers to a DNA sequence that comprises control and coding sequences necessary for the production of a polypeptide or precursor thereof. The polypeptide can be encoded by a full length coding sequence or by any portion of the coding sequence so long as the desired enzymatic activity is retained.

The term "subject" refers to animals, including humans. The subject can also be a pediatric human patient.

The term "wild-type" or "native" with reference to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "variant" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product. "Native" can also refer to the metal cofactor for an arginase, which is manganese.

VIII. Kits

Kits, such as therapeutic kits, are also provided for. For example, a kit may comprise one or more pharmaceutical composition as described herein and optionally instructions for their use. Kits may also comprise one or more devices for accomplishing administration of such compositions. For example, a subject kit may comprise pre-filled ampoules of a stabilized multimeric arginase or isolated pegylated arginase, optionally formulated as a pharmaceutical, or lyophilized, for use with a delivery device, for example, or a preloaded syringe for subcutaneous or intravenous injection of the composition into a subject.

Kits may comprise a container with a label. Suitable containers include, for example, bottles, vials, and test tubes. The containers may be formed from a variety of materials such as glass or plastic. The container may hold a composition which includes an antibody that is effective for therapeutic or non-therapeutic applications, such as described above. The label on the container may indicate that the composition is used for a specific therapy or non-therapeutic application, and may also indicate directions for either in vivo or in vitro use, such as those described above. An exemplary kit can comprise the container described above and one or more other containers comprising materials desirable from a commercial and user standpoint, including buffers, diluents, filters, needles, syringes, and package inserts with instructions for use.

EXAMPLES

The following examples serve to illustrate certain aspects of the compounds, compositions, pharmaceutical compositions and methods of use, and are not to be construed as limiting the scope thereof. In the experimental disclosure which follows, the following abbreviations apply: eq (equivalents); M (Molar); μM (micromolar); mM (millimolar); N (Normal); mol (moles); mmol (millimoles); μmol (micromoles); nmol (nanomoles); g (grams); mg (milligrams); μg (micrograms); L (liters); ml (milliliters); μl (microliters); cm (centimeters); mm (millimeters); μm (micrometers); nm (nanometers); EC (degrees Centigrade); MW (molecular weight); PBS (phosphate buffered saline); min (minutes).

Example 1

Incorporating and Determining Metal Content in Arginase I

Incorporation of $Mn^{2+}$ and $Co^{2+}$ can be achieved by purifying arginase, followed by an incubation step with 10 mM metal at 50° C. for 10 minutes. In order to determine the final metal content and identity of the arginase preparations, protein samples of Mn-hArgI (145 μM), Co-hArgI (182 μM) and associated dialysis buffers (100 mM Hepes, pH 7.4) were diluted in 2% nitric acid and analyzed by inductively coupled plasma mass spectrometry (ICP-MS, Department of Geological Sciences, University of Texas at Austin) to quantify the protein's cobalt, iron, manganese and zinc content by subtracting the concentration of metals found in the dialysis buffer from the metal concentration of the final protein samples and dividing by protein concentration. To determine protein concentrations, an extinction coefficient was calculated for hArgI based on the amino acid sequence (Gill and von Hippel, 1989). All protein concentrations for Arginase I were calculated based upon the calculated $\varepsilon_{280}$=24,180 $M^{-1}$ $cm^{-1}$ in a final buffer concentration of 6 M guanidinium hydrochloride, 20 mM phosphate buffer, pH 6.5. For comparison, arginase concentration was also calculated by BCA assay using dilutions of BSA as a standard. Using this method it was found that arginase samples incubated with $Co^{2+}$ contain 2.1±0.5 equivalents Co and 0.4±0.1 equivalents Fe, with no detectable amounts of Zn or Mn. Samples incubated with $Mn^{2+}$ contain 1.5±0.2 equivalents Mn and 0.4±0.1 equivalents Fe, and no detectable amounts of Zn or Co. Thus, heat incubation is an efficient method for incorporation of cobalt.

Additional studies of cobalt loading have demonstrated that a higher proportion of cobalt loading is achievable and results in a higher specific activity. The results of these studies is shown on the following table and in FIG. 3.

TABLE 2

Co-Arginase I Cobalt Loading

| Identity | Co (mM) | Temp (° C.) | Time (Min) | Total Co (μg/mg Arginase) | Total Mn (μg/mg Arginase) | Specific Activity (U/mg) |
|---|---|---|---|---|---|---|
| APO-Arginase I* | NA | NA | NA | <0.025 | 0.008 | 24 |
| APO Loading 1* | 0.1 | 5 | 15 | 0.3 | ND | 117 |
| Coh-Arg I* | 10 | 20 | 60 | 2 | 0.06 | 410 |
| APO Loading 2* | 1 | 5 | 15 | 2.4 | ND | 395 |
| APO Loading 3* | 10 | 20 | 15 | 2.8 | ND | 493 |
| APO Loading 4* | 10 | 20 | 60 | 2.9 | ND | 489 |
| APO Loading 5 | 10 | 37 | 15 | 2.8 | ND | NT |
| APO Loading 6 | 10 | 53 | 15 | 2.6 | ND | NT |
| Co-ArgI-PEG | 10 | 53 | 15 | 3 | ND | 500 |
| Theoretical | | | | 3.4 | | |

Figure 2:
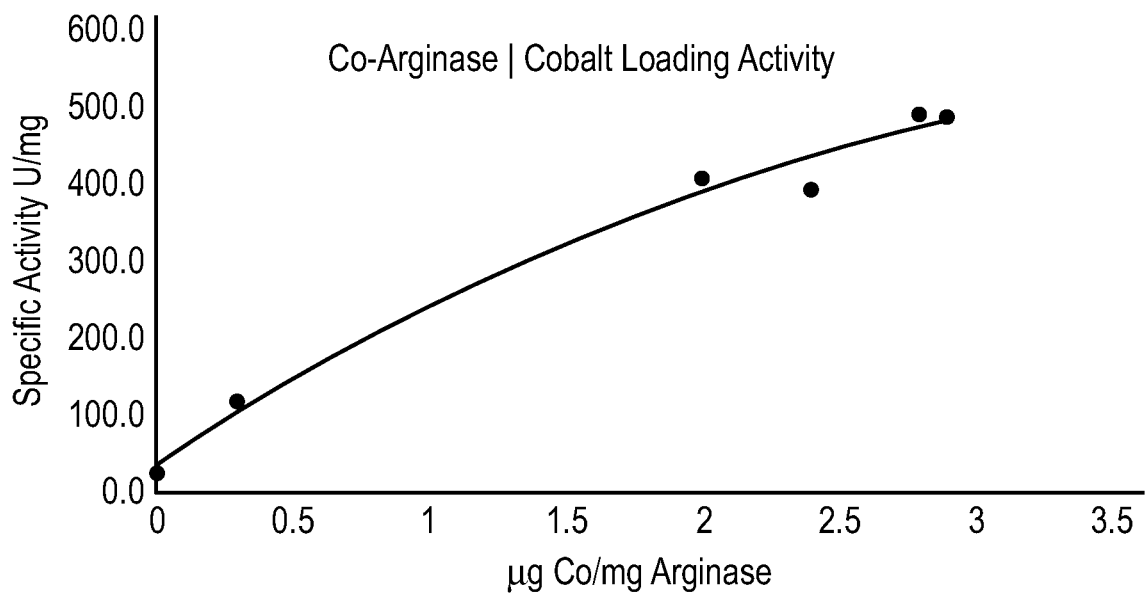
FIG. 2 is a graph showing the effect of cobalt loading on the catalytic activity of human Arginase I.

*Graphed - The starred data are shown in FIG. 2.

Example 2

Engineering an Fc-Arginase Fusion Protein for Enhanced In Vivo Half-Life

Fusion to the IgG Fc domain has been employed extensively for prolonging the in vivo half-lives of therapeutic polypeptides such as the TNF-α inhibitor etanercept (Enbrel®). The Fc domain binds to the FcγRn receptor, which is expressed on vascular endothelium and many other tissues (Roopenian and Akilesh, 2007). The affinity of FcγRn for the IgG Fc domain is strongly pH dependent. Binding occurs at the acidic pH of endosomal compartments allowing the protein to be recycled onto the cell surface and thus escape proteolytic degradation. At the cell surface, the Fc domain is released from FcγRn because the binding affinity is very low at physiological pH. Endosomal recycling via FcγRn is estimated to increase the serum half-life of immunoglobulins at least 4-7 fold, to about 7-14 days in humans. Fc fusions exploit this property to endow short lived molecules with a long half-life. However, the human arginase is a homotrimer and therefore if fused to the IgG Fc, which itself is a dimer, the resulting Fc-arginase polypeptide will likely form high molecular weight aggregates.

This problem was avoided by employing mutant forms of arginase that disrupt trimerization and are stable in the monomeric form. The trimerization and subunit interface of Arginase I have been studied in some detail (Lavulo et al., 2001). A single amino acid substitution at Glu256Gln has been shown to disrupt trimerization resulting in the formation of monomeric Arginase I enzyme (Sabio et al., 2001). After expression and purification of this variant, the steady-state kinetic analysis revealed nearly identical activity compared to Co-hArgI with a $k_{cat}/K_M$ of 1,320 $s^{-1}$ $mM^{-1}$.

This construct was then cloned into Fc expression vectors. The Fc expression vector is a construct based on a pTRC99a plasmid (Amersham) that contains a DsbA leader sequence followed by the IgG Fc coding region, an EcoRI restriction site and a stop codon. The monomeric arginase gene was placed in frame behind the Fc coding region by digesting both vector and gene with EcoRI, and was subsequently ligated and transformed into *E. coli* (BL21) for sequencing and expression. Since the IgG Fc is normally a glycosylated protein, expression of recombinant IgGs or of Fc fusions has so far been carried out in recombinant mammalian cells that, unlike bacteria, are capable of N-linked glycosylation. However, while glycosylation at Asn297 is critical for the binding to the activating and inhibitory Fcγ receptors (FcγRI-III in humans), it does not have a noticeable effect on the affinity or pH dependent binding to FcγRn (Tao and Morrison, 1989; Simmons et al., 2002). Thus, aglycosylated IgG antibodies expressed in bacteria exhibit serum persistence in primates nearly indistinguishable from that of fully glycosylated antibodies expressed in mammalian cells (Simmons et al., 2002). In contrast to prevailing earlier notions, IgG antibodies and Fc proteins can be expressed efficiently in *E. coli* up to g/L levels in fermenters. *E. coli* expression is technically much simpler and faster. In addition, since the resulting protein is aglycosylated, it does not display glycan heterogeneity, an important issue in the expression of therapeutic glycoproteins (Jefferis, 2007). The fusion protein is purified by Protein A chromatography and the yield of correctly folded, dimeric Fc-arginase fusion relative to polypeptides that fail to dimerize is quantified by FPLC gel filtration chromatography. This formulation has led to a highly active and very stable form of human arginase, suitable for in vivo trials.

Example 3

Pegylation of Arginase

Arginase I (SEQ ID NO: 3) was purified and was then made 10 mM with $CoCl_2$ and heated at 50° C. for 10 minutes. After centrifuging to remove any precipitates, the PEG-5000 arginase was extensively buffer exchanged (PBS with 10% glycerol) using a 100,000 MWCO filtration device (Amicon), and sterilized with a 0.2 micron syringe filter (VWR). All pegylated enzyme was analyzed for lipopolysaccharide (LPS) content using a Limulus Amebocyte Lysate (LAL) kit (Cape Cod Incorporated).

Pegylated Co-hArgI was found to have nearly identical serum stability to wild type enzyme and displayed a $k_{cat}/K_m$ value of $1690\pm290$ $s^{-1}$ $mM^{-1}$.

Pegylated arginase I preparation in combination with cobalt is further described in U.S. Pat. No. 8,679,479, which is incorporated herein by reference.

Example 4

Serum Depletion of L-Arg in the Mouse Model

Balb/c mice were treated by single IP injection with 500 μg of pharmacologically prepared, pegylated Co-hArgI or an equal volume of PBS. Mice were sacrificed by cardiac veni-puncture for blood collection at the time points of 0, 48, 72, and 96 hrs. Blood samples were immediately mixed 50:50 (v/v) with a 400 mM sodium citrate buffer pH 4, allowed to clot for 30 minutes and centrifuged for serum separation. The resulting serum was then filtered on a 10,000 MWCO device (Amicon) for the removal of large proteins and precipitates and the flow-through was collected for analysis. L-arginine standards, control mouse serum and experimental samples were derivatized with OPA (Agilent) and separated on a C18 reverse phase HPLC column (Agilent) (5 μm, 4.6×150 mm) essentially as described by Agilent Technologies (Publication Number: 5980-3088) except for modification of the separation protocol slightly by reducing the flow rate by ½ and doubling the acquisition time to get better peak separation. An L-arginine standard curve was constructed by plotting L-Arg peak area versus concentration in order to quantify serum L-Arg levels. A single dose of pharmacologically prepared Co-hArgI was sufficient to keep L-Arg at or below detection limits for over 3 days (FIG. 1).

Example 5

Subcutaneous and Intravenous Administration of Arginase

Single intravenous (IV) or subcutaneous (SC) doses of AEB1102 (Arginase 1 lacking the N-terminal methionine in SEQ ID NO: 3, having cobalt as the cofactor and pegylated) were administered to male cynomolgus monkeys. The purpose of this study was to characterize the pharmacokinetics (PK) and pharmacodynamics (PD) of modified arginase I (AEB1102) after IV versus SC dosing.

Following IV administration at 0.5 mg/kg dose, exposure to AEB1102 was achieved. The observed volume of distribution (Vss) was similar to monkey serum volume (45 mL/kg) and the resulting half-life (T½) was 37.0±1.79 hr. Intravenous administration of AEB1102 at 0.5 mg/kg led to maximal arginine suppression at 24 hr post dose. Below limit of quantification (BQL) levels of arginine were only achieved in 2 out of three animals in this dose group. Arginine recovery appeared to coincide with AEB1102 levels dropping below a mean (±SD) concentration of 7.25±0.433 μg/mL. Recovery to pre-dose levels of arginine was incomplete at 168 hr post dose.

Following SC administration of AEB1102 at 0.5 mg/kg dose in 2 separate formulations, the mean concentration profiles were overlapping for Groups 2 and 3 although there was a trend for slightly higher 24 hr concentrations in Group 3 and absorption appeared slightly faster for this group. Median Tmax was identical for the two groups at 24 hr. The SC T½ estimates appeared slightly shorter for Group 3 (38.1±1.00 hr) vs. Group 2 (46.5±3.05 hr). SC administration at 0.5 mg/kg led to notable arginine suppression for both formulations of AEB1102 in Groups 2 and 3. Maximal (incomplete) suppression of arginine was achieved in most of the SC animals at 24 hr post dose. Arginine recovery appeared to coincide with AEB1102 levels dropping below ~3.6 to ~4.6 μg/mL. Recovery to pre-dose levels of arginine was incomplete at 168 hr post dose.

For Group 1, test article was pre-formulated at a nominal concentration of 3 mg/mL in phosphate-buffered saline (PBS) with 10% glycerol, pH 7.4 (GMP Lot 02) and was used as received. The Group 2 test article was received as a pre-formulated stock solution at 70 mg/mL in 20 mM potassium phosphate, 37.5 mM NaCl, 5.6% sucrose and 0.02% PS80, pH 6.7 (Lot #144350-0004). This stock was diluted to 20 mg/mL (in PBS) prior to dosing. The Group 3 test article was received in prefilled syringes with a solution containing 562.5 mg/mL Triacetin, ~387 mg/mL sucrose, and 20.7 mg/mL AEB1102 (active; Lot #170315P24). The syringes were used as received.

TABLE 3

Experimental Design

| Group | Test Article | No. of Males | Route of Admin. | Dose (mg/kg) | Dose Volume (mL/kg) | Vehicle |
|---|---|---|---|---|---|---|
| 1 | AEB1102 | 3 | IV | 0.5 | 0.167 | A |
| 2* | AEB1102 | 3 | SC | 0.5 | 0.025 | C |
|  | Saline Control |  |  | 0 | 0.025 |  |

TABLE 3-continued

Experimental Design

| Group | Test Article | No. of Males | Route of Admin. | Dose (mg/kg) | Dose Volume (mL/kg) | Vehicle |
|---|---|---|---|---|---|---|
| 3* | AEB1102 Saline Control | 3 | SC | 0.5 0 | 0.025 0.025 | B |

"*": For Groups 2 and 3, each animal received 2 SC injections at each dosing interval, i.e., administration of test article and administration of 0.5% Sodium Chloride for Injection, USP, at separate sites. Both injection sites were marked. Test article and control were administered once weekly for 4 consecutive weeks.
"A": 10% glycerol in PBS, pH 7.4;
"B": 562.5 mg Triacetin, 386.89 mg sucrose and 50.61 mg AEB1102 (20.7 mg active) per 1 mL formulation; and
"C": 20 mM potassium phosphate, 37.5 mM NaCl, 5.6% sucrose, and 0.02% PS80, pH 6.7.

The animals in Group 1 received a single IV dose. These doses were administered as bolus injections via the saphenous (or other suitable) vein. If a catheter was used for dosing, the catheter was immediately flushed with ~1 mL of sterile Sodium Chloride for Injection, USP, following dosing.

The animals in Groups 2 and 3 received once weekly SC doses of AEB1102 for four consecutive weeks. In addition, these animals received SC injections of saline control at a separate location which was administered with the same dosing frequency and dosing volume as the test article. The SC doses were administered as bolus injections between the skin and the underlying layers of tissue in the scapular region on the back of each animal. The injection sites were marked following dosing and were re-marked as needed.

The following PK and PD blood samples were collected: pre-dose; and 1, 4, 8, 24, 48, 72, 96, 120, 144, and 168 hours post-dose. Blood (1 mL/time point) for PK was collected from the femoral vein/artery (or other suitable vein) into tubes with no anticoagulant. Samples were allowed to clot at room temperature, and subsequent to centrifugation, the serum samples were split into two aliquots and stored frozen (−60 to −90° C.) until analysis. Blood (1 mL/time point) for PD was collected from the femoral vein/artery (or other suitable vein) into pre-chilled EDTA SCAT tubes and immediately placed on ice. Subsequent to centrifugation under refrigerated conditions, the resultant plasma (0.4 mL) had 8 µL of acetic acid added, and the aliquot was mixed by inversion of the tube. If the plasma volume per aliquot was less than 0.4 mL (2 aliquots targeted), the added volume of acetic acid was adjusted to achieve a final concentration of at least 2% (v/v) acetic acid. The aliquots were stored frozen (−60 to −90° C.) until analysis.

Quantitation Assays:

Analysis for serum AEB1102 concentrations was performed at Intertek Pharmaceutical Services using a validated enzyme activity assay (Bioanalytical Procedure No. BPAEB1102D) in nonhuman primate serum. The lower limit of quantitation (LLOQ) was 0.125 µg/mL in 100% serum. Analysis for plasma arginine concentrations also was performed at Intertek Pharmaceutical Services using a validated LC-MS/MS assay (Bioanalytical Procedure No. BPARGN1) in nonhuman primate plasma. The LLOQ was 1 µM in 100% plasma.

Pharmacokinetic Analysis

Serum AEB1102 concentration versus time data, obtained in a Microsoft Excel (Excel; Microsoft Corp., Seattle, WA) spreadsheet from Intertek Pharmaceutical Services, were analyzed by noncompartmental analysis (NCA) with Phoenix™ WinNonlin® Version 7.0 (WinNonlin; Certara USA, Inc., Mountain View, California), using an IV bolus or an extravascular administration model as appropriate. Nominal doses and blood collection times were used in the NCA.

For the IV dose groups, all BQL concentrations were set to missing; this convention allowed for more accurate back-extrapolation and calculation of the serum concentration immediately after injection (C0). For the SC dose groups, BQL concentrations prior to Cmax were set to 0 while BQL concentrations after Cmax were excluded from the PK analysis.

The area under the curve from time zero to the last measurable concentration (AUC0-t) was calculated by the linear up/log down method. Log/linear regression through the last three or more time points (excluding Tmax) was used to estimate the elimination constant ($\lambda z$). The terminal phase half-life (T½) and the AUC from time zero to infinity (AUC0-∞) were calculated using the following equations:

$$T\textonehalf = \ln(2)/\lambda z$$

$$AUC0\text{-}\infty = AUC0\text{-}t + Ct,\text{pred}/\lambda z,$$

where Ct,pred is the last concentration as predicted by the slope of the terminal phase selected by WinNonlin. The reported PK parameters are listed in the table below along with a brief definition.

Parameter Description:
  Cmax: The maximum observed concentration of drug measured after dosing.
  Tmax: The time after dosing at which the maximum observed concentration of drug was observed.
  Tlast: The time after dosing at which the last measurable concentration of drug was observed.
  AUC0-t: The area under the drug concentration versus time curve from time zero to the time after dosing at which the last measurable concentration of the drug was observed.

When data permitted, the slope of the terminal elimination phase of each concentration versus time curve was determined by log/linear regression, and the additional parameters listed below were also estimated. The goodness of fit (R2) of the slope of the regression line had to be greater than or equal to 0.8 for reporting of the following data dependent on the terminal phase.

Additional Parameters:
  T½: The apparent terminal elimination half-life.
  AUC0-inf (or AUC0-∞): The area under the concentration versus time curve from time zero to infinity.
  CL: The volume of serum cleared of drug per unit time following a single IV dose.
  CL/F: The apparent volume of serum cleared of drug per unit time following a single SC dose.
  Vss: Volume of distribution at steady-state after IV administration.
  Vz: Terminal phase volume of distribution after IV administration.
  Vz/F: Apparent terminal phase volume of distribution after SC administration.
  F: Bioavailability or percent of dose absorbed after SC administration.

Bioavailability (F) after SC administration was evaluated using the following equation:

$$F = 100\% * (AUC0\text{-}\infty,SC/DoseSC)/(AUC0\text{-}\infty,IV/DoseIV)$$

Pharmacodynamic Analysis:

Arginine concentration versus time data were obtained in an Excel spreadsheet from Intertek Pharmaceutical Services and plotted with the corresponding AEB1102 concentrations using GraphPad Prism Version 7.0 (GraphPad Software, La Jolla, CA).

Statistical Analysis

Summary statistics [N, mean, standard deviation (SD), minimum (Min), median (Med), maximum (Max), coefficient of variability (CV)] for the PK parameters and the concentration data were prepared with WinNonlin. When less than 50% of the monkeys had measurable concentrations, the Min, and Med were presented as BQL, and the Max was the highest measurable concentration while the mean, SD and % CVs were not reported. When at least 50% of the monkeys had measurable concentrations, the summary statistics were solely based on the measurable concentrations. When all of the subjects had BQL concentrations, the mean, Min, Med, and Max were presented as BQL, and SD and % CV were not reported. Graphs were generated with GraphPad Prism (Version 7.00 for Windows, GraphPad Software, San Diego California).

IV administration of AEB1102 at 0.5 mg/kg led to maximal arginine suppression at 24 hr post dose. BQL levels of arginine were only achieved in 2 out of three animals in this dose group. Arginine recovery appeared to coincide with AEB1102 levels dropping below a mean (±SD) concentration of 7.25±0.433 µg/mL. Recovery to pre-dose levels of arginine was incomplete at 168 hr post dose.

Following SC administration of AEB1102 in 2 separate formulations, the mean concentration profiles were overlapping for Groups 2 and 3 although there was a trend for slightly higher 24 hr concentrations in Group 3 and absorption appeared slightly faster for this group. Median Tmax was identical for the two groups at 24 hr. The SC T½ estimates appeared slightly shorter for Group 3 (38.1±1.00 hr) vs. Group 2 (46.5±3.05 hr).

SC administration at 0.5 mg/kg led to notable arginine suppression for both formulations of AEB1102 in Groups 2 and 3. Maximal (incomplete) suppression of arginine was achieved in most of the SC animals at 24 hr post dose. Arginine recovery appeared to coincide with AEB1102 levels dropping below ~3.6 to ~4.6 µg/mL. Again, recovery to pre-dose levels of arginine was incomplete at 168 hr post dose.

Figure 3:
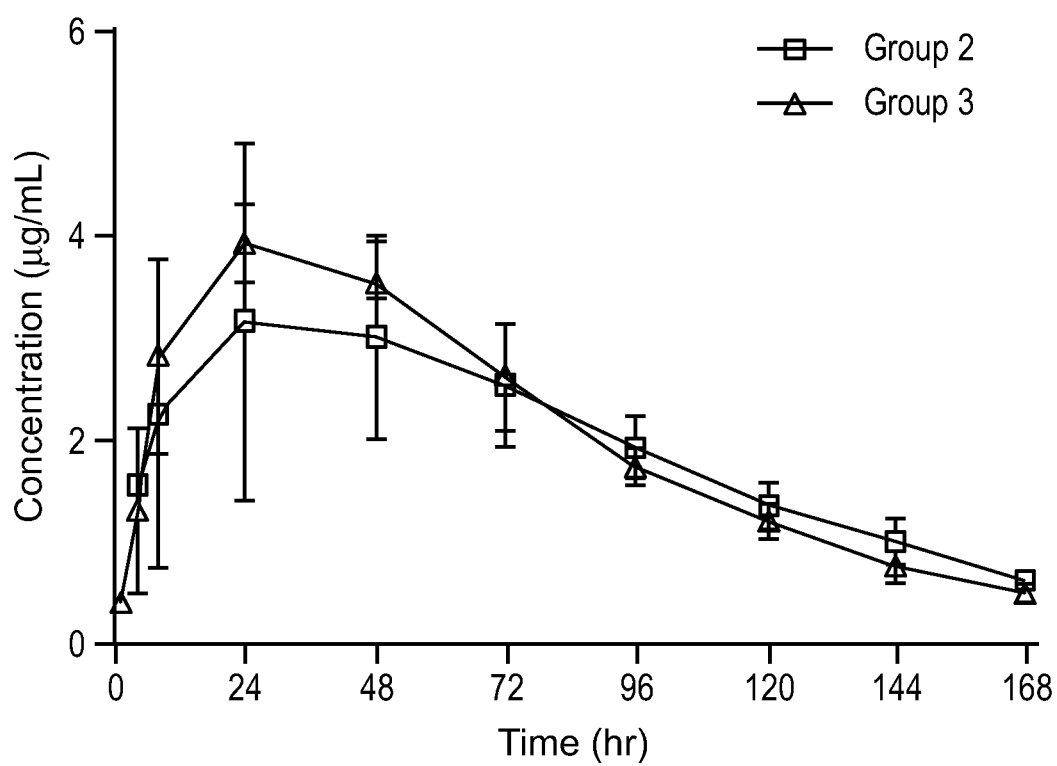
FIG. 3 is a graph of mean (±SD) concentration vs. time profiles for AEB1102 in male monkeys after a single 0.5 mg/kg IV dose.

Pharmacokinetics:

The mean PK parameters in male monkeys following IV administration of AEB1102 are summarized in Table 4 while the mean serum concentration versus time profile is presented in FIG. 3.

TABLE 4

Mean (±SD) PK Parameters for AEB1102 in Male Monkeys After a Single 0.5 mg/kg IV Dose

| Stat. Param. | $T_{1/2}$ (hr) | $T_{max\ 1}$ (hr) | $C_{max}$ (µg/mL) | $AUC_{0-t}$ (hr*µg/mL) | $AUC_{0-\infty}$ (hr*µg/mL) | $V_z$ (mL/kg) | CL (mL/hr/kg) |
|---|---|---|---|---|---|---|---|
| N | 3 | 3 | 3 | 3 | 3 | 3 | 3 |
| Mean | 37.0 | 1.0 | 11.9 | 576 | 604 | 44.2 | 0.829 |
| SD | 1.79 | 1.0, 1.0 | 0.265 | 19.1 | 27.4 | 0.142 | 0.0369 |
| CV % | 4.9 | NA | 2.2 | 3.3 | 4.5 | 0.3 | 4.4 |

1: Median and range (Min, Max) presented; NA: not applicable.

Figure 4:
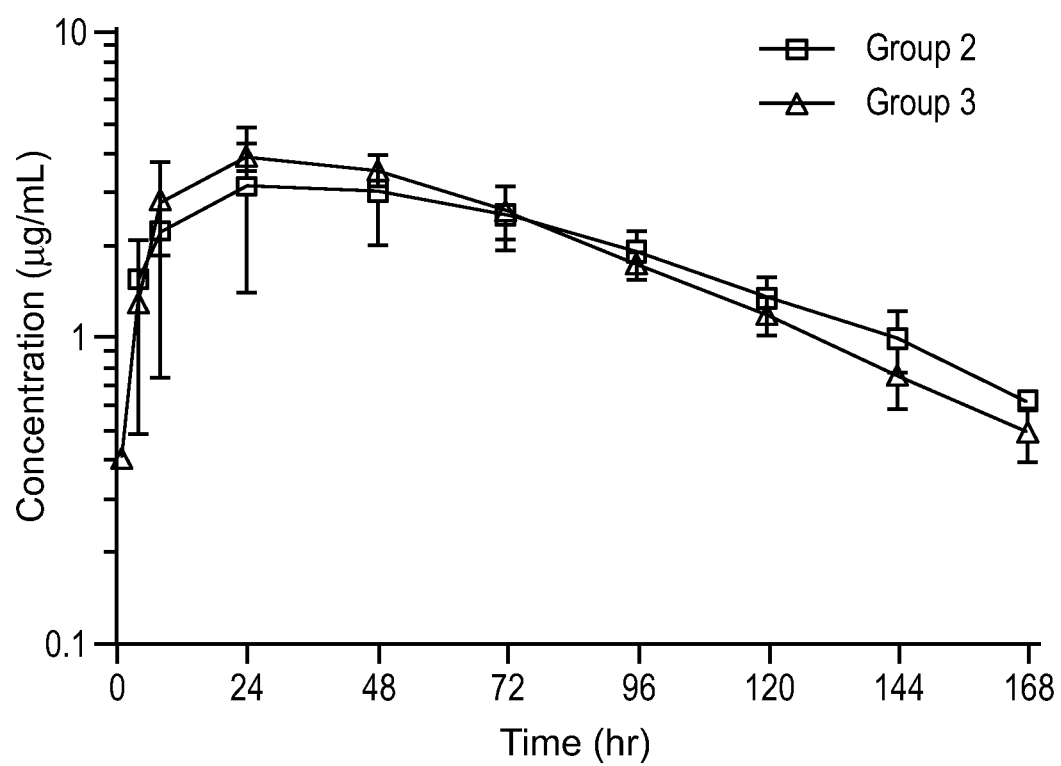
FIG. 4 is a graph of mean (±SD) concentration vs. time profiles for AEB1102 in male monkeys after a single 0.5 mg/kg SC dose. AEB1102 is a pegylated human arginase I having the sequence SEQ ID NO: 3 that lacks the N-terminal methionine and having Co$^{+2}$ as the metal co-factor.

The mean PK parameters in male monkeys following SC administration of AEB1102 are summarized in Table 5 while the mean serum concentration versus time profile is presented in FIG. 4.

TABLE 5

Mean (±SD) PK Parameters for AEB1102 in Male Monkeys After a Single 0.5 mg/kg SC Dose

| Group | Stat. Param. | T½ (hr) | Tmax 1 (hr) | Cmax (µg/mL) | $AUC_{0-t}$ (hr*µg/mL) | AUC0-∞ (hr*µg/mL) | Vz/F (mL/kg) | CL/F (mL/hr/kg) | F (%) |
|---|---|---|---|---|---|---|---|---|---|
| 2 | N | 3 | 3 | 3 | 3 | 3 | 3 | 3 | 3 |
| 2 | Mean | 46.5 | 24 | 3.38 | 331 | 375 | 96.4 | 1.42 | 62.0 |
| 2 | SD | 3.05 | 24, 48 | 1.39 | 106 | 108 | 37.4 | 0.454 | 17.8 |
| 2 | CV % | 6.6 | NA | 41.2 | 32.0 | 28.8 | 38.7 | 32.0 | 28.7 |
| 3 | N | 3 | 3 | 3 | 3 | 3 | 3 | 3 | 3 |
| 3 | Mean | 38.1 | 24 | 3.92 | 351 | 379 | 73.6 | 1.34 | 62.7 |
| 3 | SD | 1.00 | 24, 48 | 0.382 | 53.4 | 59.3 | 8.96 | 0.194 | 9.82 |
| 3 | CV % | 2.6 | NA | 9.7 | 15.2 | 15.7 | 12.2 | 14.5 | 15.6 |

1: Median and range (Min, Max) presented; NA: not applicable.

A comparison of FIG. 3 with FIG. 4 demonstrates the difference in Arginase 1 (AEB1102) enzyme levels in intravenous administration as compared to the subcutaneous route. In FIG. 3, upon IV administration, the drug is at its highest concentration after only 1 hour, while the Tmax for the SC dose is 24 hours for the SC Groups. It is contemplated that the very rapid increase in drug level with an IV administration could be responsible for adverse events in a subject, particularly a pediatric subject.

Pharmacodynamics

Figure 5A:
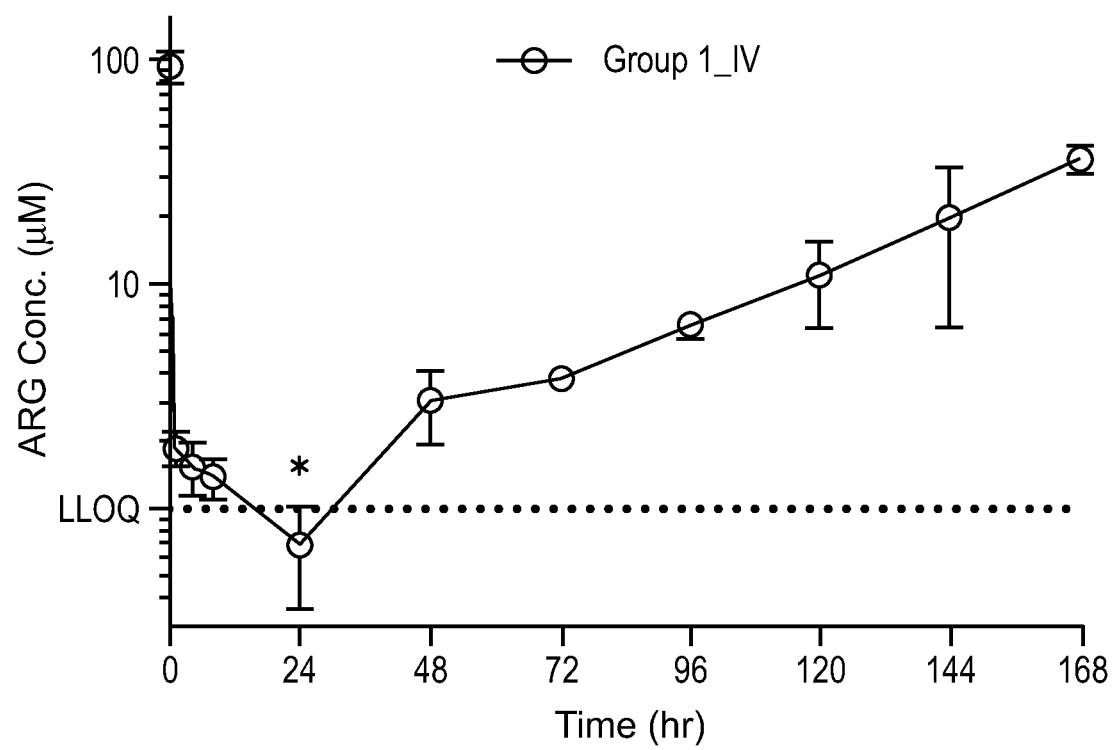
FIG. 5A is a graph of mean (±SD) pharmacodynamic profiles in male monkeys after a single 0.5 mg/kg IV dose of AEB1102.
Figure 5B:
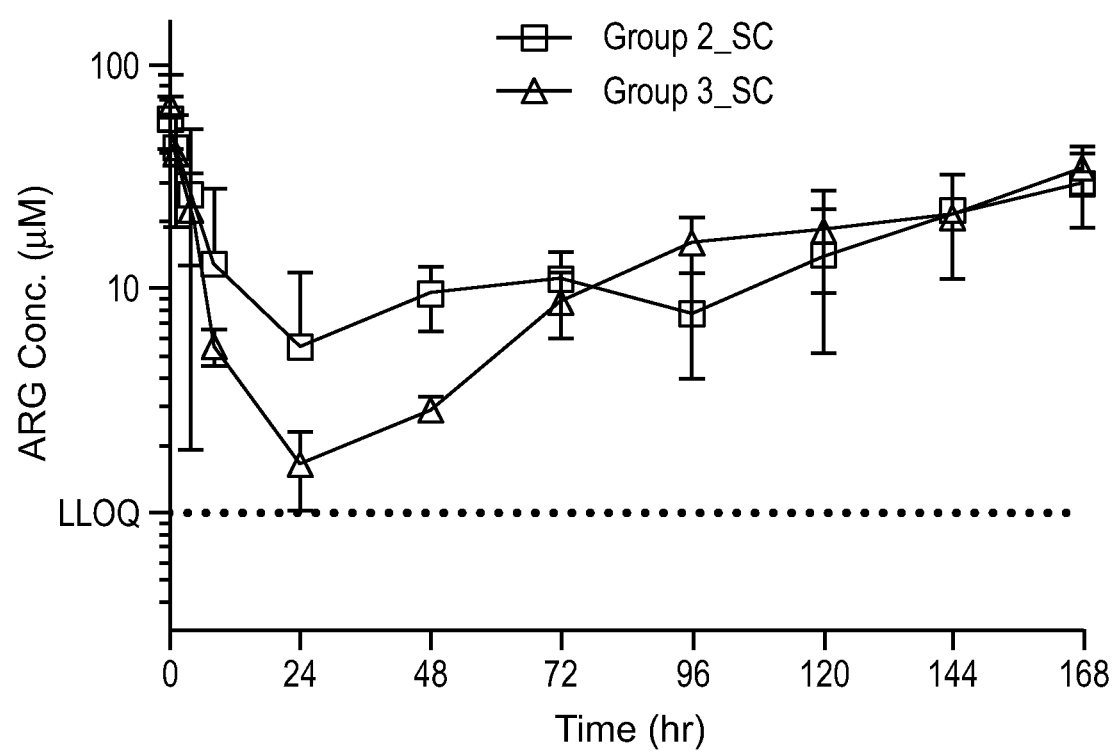
FIG. 5B is a graph of mean (±SD) pharmacodynamic profiles in male monkeys after a single 0.5 mg/kg SC dose of AEB1102.

The mean pharmacodynamic profiles in male monkeys after a single dose of 0.5 mg/kg IV or SC is shown in FIG. 5.

The left hand panel of FIG. 5 shows a rapid drop in arginine levels by up to approximately 98% within the first hour and continue to drop below the lower limit of quantitation by 24 hours. In contrast, the SC dose can result in a less dramatic decrease in arginine levels in the first hours after administration, reaches a higher minimum concentration than the IV dose and also provides a longer window of therapeutic efficacy.

Example 6

In Vivo Experiment for Arginase Reduction of GAA levels in a GAMT-/- Mouse Model The goal of the experiment is to confirm whether AEB1102 can reduce GAA levels in a GAMT-/- mouse model thereby providing evidence supporting the use of an arginine depleting enzyme for the treatment of GAMT deficient patients.

GAMT-/- and wild-type C57BL/6J mice were maintained on a creatine deficient diet. Mice were administered via the intraperitoneal route of administration either PBS or AEB1102 at 2 mg/kg. After 72 hours, the mice were sacrificed and their blood collected into Nor-NOHA containing tubes. GAA, ornithine and arginine levels were measured according to Tran et al. (2014).

Arginase i.p. treatment in the GAMT-/- mouse model causes a decrease of arginine (e.g., 75.6 µM to 26.2 µM) and a concomitant increase of ornithine in both wild type and GAMT-/- mice. As expected, the GAA levels were very low (1.9 to 0.0 µM) in the wild type mice, but significantly elevated in the GAMT-/- mice as depicted in the Table below. AEB1102 treatment resulted in an approximate 30 µM decrease in the mean GAA plasma levels over the negative control animal 67.3 to 38.6 in for the mean). The data represents the mean±SEM. The number of animals in each group is signified by "n" and SEM is the standard error of the mean.

All of the compositions and methods of use disclosed and claimed herein can be made and executed without undue experimentation in light of the present disclosure. While the compositions and methods have been described in terms of preferred or exemplary embodiments, it will be apparent to those of skill in the art that variations may be applied to the compositions and methods, and in the steps or in the sequence of steps of the methods described herein without departing from the concept, spirit and scope of the described materials and methods. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the compositions and methods as further set forth in the appended claims.

1. A method of treating a deficiency in guanidinoacetate methyltransferase (GAMT) activity in a subject, comprising administering to said subject a pharmaceutical composition comprising a therapeutic amount of an arginine depleting enzyme.

2. The method of claim 1, wherein the arginine depleting enzyme is a mammalian or a bacterial arginase enzyme.

3. The method of claim 1, wherein the arginine depleting enzyme is a human arginine depleting enzyme.

4. The method of claim 1, wherein the arginine depleting enzyme is a human arginase enzyme, a human arginine deiminase enzyme or a combination thereof.

5. The method of 4, wherein one or more of the human arginase enzyme or human arginine deiminase enzyme is modified by a substitution, a deletion, an insertion, or a truncation in the amino acid sequence of the enzyme.

6. The method of claim 1, wherein the pharmaceutical composition comprises a human Arginase I enzyme or human Arginase II enzyme.

7. The method of claim 1, wherein the arginine depleting enzyme is a human Arginase I enzymes.

8. The method of any of claim 6 or 7, wherein the human Arginase I enzyme is engineered with a substituted metal cofactor comprising cobalt.

9. The method of claim 2, wherein the arginine depleting enzyme is administered in an autologous red blood cell ghost.

10. The method of claim 1, wherein the deficiency in GAMT activity is associated with a genetic deficiency in a gene encoding a guanidinoacetate methyltransferase enzyme in said subject.

11. The method of claim 4, wherein the human arginase enzyme or human arginine deiminase enzyme is stabilized by association with a stabilizing agent.

TABLE 6

Displaying Data from Mouse GAMT-/- Model (values are presented in µM)

| Mouse Type | Therapy | Arginine (Mean) | Arginine (SEM) | Ornithine (Mean) | Ornithine (SEM) | GAA (Mean) | GAA (SEM) |
|---|---|---|---|---|---|---|---|
| GAMT-/- | PBS (n = 3) | 75.6 | 14.7 | 32.3 | 9.2 | 67.3 | 9.3 |
| | AEB1102 (n = 5) | 26.2 | 18.9 | 77.4 | 11.0 | 38.6 | 3.9 |
| Wild Type | PBS (n = 3) | 87.6 | 5.6 | 49.2 | 7.9 | 1.9 | 0.0 |
| | AEB1102 (n = 5) | 9.6 | 1.7 | 82.2 | 12.8 | 0.7 | 0.1 |

12. The method of claim 11, wherein the stabilizing agent is selected from the group consisting of: a polyethylene glycol (PEG), a synthetic protein polymer, a polysialic acid, an Fc fusion, and albumin.

13. The method of any of claims 6-8, wherein the human Arginase I enzyme is pegylated.

14. The method of any of claims 1-13, wherein the subject is a human.

15. The method of claim 7, wherein the human Arginase I enzyme displays a $k_{cat}/K_M$ for the hydrolysis of arginine of between 400 mM$^{-1}$ s$^{-1}$ and 4,000 mM$^{-1}$ s$^{-1}$ at pH 7.4 and 37° C. when measured in vitro.

16. The method of claim 8, wherein the human Arginase I enzyme comprises a ratio of cobalt to arginase of from 2 μg Co/mg arginase to 3 μg Co/mg arginase.

17. The method of claim 8, wherein the human Arginase I enzyme is produced by contacting an arginase apoenzyme with cobalt or a cobalt ion at a temperature of from 30° C. to 55° C. for 15 minutes to 60 minutes.

18. A method of treating effects of guanidinoacetate (GAA) toxicity in a subject with a deficiency in guanidinoacetate methyltransferase (GAMT) activity, comprising administering to said subject a therapeutic amount of a pharmaceutical composition comprising a pegylated human Arginase I enzyme comprising a cobalt cofactor.

19. The method of claim 18, wherein administration continues until said subject exhibits improvement in a physical or neurological condition.

20. The method of claim 19, wherein said physical or neurological condition comprises at least one of condition selected from the group consisting of: a global developmental delay/intellectual disability (DD/ID), epilepsy, a movement disorder, a speech or language delay, and a behavioral disorder.

21. The method of claim 18, wherein the therapeutic amount of the pegylated human Arginase I enzyme comprising a cobalt cofactor is from about 0.01 mg/kg to about 7.5 mg/kg.

22. The method of claim 18, wherein the therapeutic amount of the pegylated human Arginase I enzyme comprising a cobalt cofactor is from about 0.05 mg/kg to about 5 mg/kg.

23. The method of claim 18, wherein the therapeutic amount of the pegylated human Arginase I enzyme comprising a cobalt cofactor is from about 0.1 mg/kg to about 5 mg/kg.

24. The method of claim 18, wherein the pharmaceutical composition is administered parenterally to said subject.

25. The method of claim 18, wherein the pharmaceutical composition is administered topically, intravenously, intradermally, intraarterially, intraperitoneally, intralesionally, intracranially, intraarticularly, intraprostaticaly, intrapleurally, intratracheally, intraocularly, intranasally, intravitrreally, intravaginally, intrarectally, intramuscularly, subcutaneously, subconjunctival, intravesicularlly, mucosally, intrapericardially, intraumbilically, orally, by inhalation, by injection, by infusion, by continuous infusion, by localized perfusion bathing target cells directly, via a catheter, or via a lavage.

26. The method of claim 18, wherein the pharmaceutical composition is adapted for subcutaneous administration to the subject.

27. The method of claim 26, wherein the pharmaceutical composition comprises a therapeutic dose of an arginase in potassium phosphate, NaCl, sucrose, and PS80 at pH 6.7.

28. A kit for use in the method of claim 18, wherein said kit comprises a syringe containing a solution comprising Triacetin, sucrose, and the pegylated human Arginase I enzyme adapted for subcutaneous administration.

29. The method of claim 18, wherein the pharmaceutical composition is adapted for intravenous administration.

30. The method of claim 29, wherein the pharmaceutical composition comprises the pegylated human Arginase I enzyme, saline, and glycerol at pH 7.4.

31. The method of claim 26, wherein administering the pharmaceutical composition reduces serum arginine in the patient by 50% to 99%.

32. The method of claim 26, wherein administering the pharmaceutical composition reduces serum arginine in the patient by 90% to 99%.

33. The method of claim 26, wherein administering the pharmaceutical composition reduces serum GAA in the patient by at least 25% to 50%.

34. The method of claim 26, wherein a concentration of the pharmaceutical composition in plasma reaches a maximum level 20 to 28 hours after a single administration.

35. The method of claim 26, wherein a concentration of the pharmaceutical composition in plasma reaches a maximum level about 24 hours after a single administration.

36. A method of treating effects of guanidinoacetate (GAA) toxicity, comprising administering to a subject in need thereof, a therapeutic amount of a pharmaceutical composition comprising an arginine depleting enzyme.

37. The method of claim 36, wherein the arginine depleting enzyme is an arginase or arginine deiminase enzyme.

38. A method of treating a deficiency in guanidinoacetate methyltransferase (GAMT) activity in a subject, comprising administering to said subject a pharmaceutical composition comprising a therapeutic amount of an arginine depleting enzyme in combination with ornithine supplementation.

39. The method of claim 38, wherein the arginine depleting enzyme is an arginase or arginine deiminase enzyme.

40. The method of claim 38, the pharmaceutical composition comprising a high-dose L-ornithine supplementation.

41. The method of claim 38, comprising orally administering L-ornithine aspartate or L-ornithine hydrochloride.

42. A pharmaceutical composition comprising a therapeutic amount of an arginine depleting enzyme for use as a medicament for use in the treatment of a deficiency in guanidinoacetate methyltransferase (GAMT) activity in a subject or treating effects of guanidinoacetate (GAA) toxicity in a subject.

43. A pharmaceutical composition comprising a therapeutic amount of an arginine depleting enzyme for use in the treatment of a deficiency in guanidinoacetate methyltransferase (GAMT) activity in a subject or treating effects of guanidinoacetate (GAA) toxicity in a subject.

44. The pharmaceutical composition of any of claims 42 and 43, wherein the arginine depleting enzyme is a mammalian or a bacterial arginase enzyme.

45. The pharmaceutical composition of any of claims 42 and 43, wherein the arginine depleting enzyme is a human arginine depleting enzyme.

46. The pharmaceutical composition of any of claims 42 and 43, wherein the human arginine depleting enzyme is a human arginase enzyme, a human arginine deiminase enzyme or a combination thereof.

47. The pharmaceutical composition of claim 46, wherein one or more of the human arginase enzyme or arginine deiminase enzyme is modified by a substitution, a deletion, an insertion, or a truncation of the amino acid sequence of the human arginase enzyme or arginine deiminase enzyme.

48. The pharmaceutical composition of any of claims 42 and 43, wherein the pharmaceutical composition comprises a human Arginase I enzyme or Arginase II enzyme.

49. The pharmaceutical composition of any of claims 42 and 43, wherein the arginine depleting enzyme comprises a human Arginase I enzyme.

50. The pharmaceutical composition of any of claim 48 or 49, wherein the arginine depleting enzyme comprises a human Arginase I enzyme engineered with a substituted metal cofactor comprising cobalt.

51. The pharmaceutical composition of claim 44, wherein the arginine depleting enzyme is administered in an autologous red blood cell ghost.

52. The pharmaceutical composition of any of claims 42 and 43, wherein the deficiency in GAMT activity is associated with a genetic deficiency in a gene encoding a guanidinoacetate methyltransferase enzyme.

53. The pharmaceutical composition of claim 46, wherein the human arginase enzyme or human arginine deiminase enzyme is stabilized by association with a stabilizing agent.

54. The pharmaceutical composition of claim 53, wherein the stabilizing agent is selected from the group consisting of: a polyethylene glycol (PEG), a synthetic protein polymer, a polysialic acid, an Fc fusion, and albumin.

55. The pharmaceutical composition of any of claims 58-60, wherein the human Arginase I enzyme is pegylated.

56. The pharmaceutical composition of any of claims 42-55, wherein the subject is a human.

57. The pharmaceutical composition of claim 49, wherein the human Arginase I enzyme displays a $k_{cat}/K_M$ for the hydrolysis of arginine of between 400 $mM^{-1}$ $s^{-1}$ and 4,000 $mM^{-1}$ $s^{-1}$ at pH 7.4 and 37° C. when measured in vitro.

58. The pharmaceutical composition of claim 50, wherein the human Arginase I enzyme comprises a ratio of cobalt to arginase of from 2 μg Co/mg arginase to 3 μg Co/mg arginase.

59. The method of claim 50, wherein the human Arginase I enzyme is produced by contacting an arginase apoenzyme with cobalt or a cobalt ion at a temperature of from 30° C. to 55° C. for 15 minutes to 60 minutes.

REFERENCES

The following references, to the extent that they provide exemplary procedural or other details supplementary to those set forth herein, are specifically incorporated herein by reference.

Cama et al., *Biochemistry*, 42: 7748-7758, 2003.
Cheng et al., *Cancer Lett.*, 224: 67-80, 2005.
Cheng et al., *Cancer Res.*, 67: 309, 2007.
Cheng et al., *Cancer Res.*, 67: 4869-4877, 2007.
Dillon et al., *Med. Sci. Monit.*, 8: BR248-253, 2002.
Dowling et al., *Cell Mol. Life. Sci.*, 65(13): 2039-55, 2008.
Durante et al., *Clin. Exp. Pharmacol. Physiol.*, 34: 906-911, 2007.
Ensor et al., *Cancer Res.*, 62: 5443-5450, 2002.
Gill and von Hippel, *Anal. Biochem.*, 182: 319-326, 1989.
Greenwald et al., *Crit. Rev. Therap. Drug Carrier Syst.*, 17: 101-161, 2000.
Harkki et al., *BioTechnology*, 7: 596-603, 1989.
Harris et al., *Clin. Pharmacokinet.*, 40(7): 539-51, 2001.
Hopwood et al., In: GENETIC MANIPULATION OF STREPTOMYCES, A LABORATORY MANUAL, The John Innes Foundation, Norwich, Conn., 1985.
Jefferis, R., *Expert Opin. Biol. Ther.*, 7: 1401-1413, 2007.
Lavulo et al., *J. Biol. Chem.*, 276: 14242-14248, 2001.
Lopez et al., *FEBS J.*, 272: 4540-4548, 2005.
Lordanescu, *J. Bacteriol*, 12: 597 601, 1975.
Marescau, B., et al., "Guanidino compound analysis as a complementary diagnostic parameter for hyperargininemia: follow-up of guanidino compound levels during therapy," *Pediatr. Res.* 27: 297-303, 1990.
Mellor et al., *Gene*, 24: 1-14, 1983.
Nathan et al., *Bioconj. Chem.*, 4: 54-62, 1993.
Nathan et al., *Macromolecules*, 25: 4476-4484, 1992.
Penttila et al., *Gene*, 61:155-164, 1987.
REMINGTON'S PHARMACEUTICAL SCIENCES, 18th Ed. Mack Printing Company, 1289-1329, 1990.
Roopenian and Akilesh, *Nat. Rev. Immunol.*, 7: 715-725, 2007.
Sabio et al., *FEBS Lett.*, 501: 161-165, 2001.
Santhanam et al., *Circ. Res.*, 101: 692-702, 2007.
Savoca et al., *Cancer Biochem. Biophys.*, 7: 261-268, 1984.
Schulze, A. et al., "Improving treatment of guanidinoacetate methyltransferase deficiency: reduction of guanidinoacetic acid in body fluids by arginine restriction and ornithine supplementation," *Mol. Genet. Metab.* 74: 413-419, 2001.
Sibakov et al., *Eur. J. Biochem.*, 145: 567-572, 1984.
Simmons et al., *J. Immunol. Methods*, 263: 133-147, 2002.
Tao et al., *J. Immunol.*, 143: 2595-2601, 1989.
Tran, C., et al., "Stable isotope dilution microquantification of creatine metabolites in plasma, whole blood and dried blood spots for pharmacological studies in mouse models of creatine deficiency," *Clin. Chim. Acta* 436C: 160-168, 2014.
Villa, C., et al., "Red blood cells: Supercarriers for drugs, biologicals, and nanoparticles and inspiration for advanced delivery systems," *Adv. Drug Deliv. Rev.* 106(Pt A): 88-103, 2016.
Ward, *Embo-Alko Workshop on Molecular Biology of Filamentous Fungi*, Helsinki, 119-128, 1989.
Zalipsky et al., *Bioconjug. Chem.*, 8: 111-118, 1997.

The invention claimed is:

1. A method of treating a deficiency in guanidinoacetate methyltransferase (GAMT) activity in a subject, comprising administering to said subject a pharmaceutical composition comprising a therapeutic amount of an arginine depleting enzyme, wherein the arginine depleting enzyme is a human arginase enzyme, a human arginine deiminase enzyme, or a combination thereof.

2. The method of claim 1, wherein the human arginase enzyme or the human arginine deiminase enzyme is modified by a substitution, a deletion, an insertion, or a truncation in the amino acid sequence of the enzyme.

3. The method of claim 1, wherein the pharmaceutical composition comprises a human Arginase I enzyme or human Arginase II enzyme.

4. The method of claim 1, wherein the arginine depleting enzyme is a human Arginase I enzyme.

5. The method of claim 3 or 4, wherein the human Arginase I enzyme is engineered with a substituted metal cofactor comprising cobalt.

6. The method of claim 1, wherein the arginine depleting enzyme is administered in an autologous red blood cell ghost.

7. The method of claim 1, wherein the deficiency in GAMT activity is associated with a genetic deficiency in a gene encoding a guanidinoacetate methyltransferase enzyme in said subject.

8. The method of claim 1, wherein the human arginase enzyme or the human arginine deiminase enzyme is stabilized by association with a stabilizing agent.

9. The method of claim 8, wherein the stabilizing agent is selected from the group consisting of: a polyethylene glycol (PEG), a synthetic protein polymer, a polysialic acid, an Fc fusion, and albumin.

10. The method of claim 3, wherein the human Arginase I enzyme is pegylated.

11. The method of claim 1, wherein the subject is a human.

12. The method of claim 4, wherein the human Arginase I enzyme displays a $k_{cat}/K_M$ for the hydrolysis of arginine of between 400 mM$^{-1}$ s$^{-1}$ and 4,000 mM$^{-1}$ s$^{-1}$ at pH 7.4 and 37° C. when measured in vitro.

13. The method of claim 5, wherein the human Arginase I enzyme comprises a ratio of cobalt to arginase of from 2 µg Co/mg arginase to 3 µg Co/mg arginase.

14. The method of claim 5, wherein the human Arginase I enzyme is produced by contacting an arginase apoenzyme with cobalt or a cobalt ion at a temperature of from 30° C. to 55° C. for 15 minutes to 60 minutes.

15. A method of treating effects of guanidinoacetate (GAA) toxicity in a subject with a deficiency in guanidinoacetate methyltransferase (GAMT) activity, comprising administering to said subject a pharmaceutical composition comprising a therapeutic amount of a pegylated human Arginase I enzyme comprising a cobalt cofactor.

16. The method of claim 15, wherein administration continues until said subject exhibits improvement in a physical or neurological condition.

17. The method of claim 16, wherein said physical or neurological condition comprises at least one condition selected from the group consisting of: a global developmental delay/intellectual disability (DD/ID), epilepsy, a movement disorder, a speech or language delay, and a behavioral disorder.

18. The method of claim 15, wherein the therapeutic amount of the pegylated human Arginase I enzyme comprising a cobalt cofactor is from about 0.01 mg/kg to about 7.5 mg/kg.

19. The method of claim 15, wherein the therapeutic amount of the pegylated human Arginase I enzyme comprising a cobalt cofactor is from about 0.05 mg/kg to about 5 mg/kg.

20. The method of claim 15, wherein the therapeutic amount of the pegylated human Arginase I enzyme comprising a cobalt cofactor is from about 0.1 mg/kg to about 5 mg/kg.

21. The method of claim 15, wherein the pharmaceutical composition is administered parenterally to said subject.

22. The method of claim 15, wherein the pharmaceutical composition is administered topically, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, subcutaneously, subconjunctival, intravesicularlly, mucosally, intrapericardially, intraumbilically, orally, by inhalation, by injection, by infusion, by continuous infusion, by localized perfusion bathing target cells directly, via a catheter, or via a lavage.

23. The method of claim 15, wherein the pharmaceutical composition is adapted for subcutaneous administration to the subject.

24. The method of claim 23, wherein the pharmaceutical composition comprises potassium phosphate, NaCl, sucrose, and PS80 at pH 6.7.

25. The method of claim 15, wherein the pharmaceutical composition is adapted for intravenous administration.

26. The method of claim 25, wherein the pharmaceutical composition comprises the pegylated human Arginase I enzyme, saline, and glycerol at pH 7.4.

27. The method of claim 23, wherein administering the pharmaceutical composition reduces serum arginine in the patient by 50% to 99%.

28. The method of claim 23, wherein administering the pharmaceutical composition reduces serum arginine in the patient by 90% to 99%.

29. The method of claim 23, wherein administering the pharmaceutical composition reduces serum GAA in the patient by at least 25% to 50%.

30. The method of claim 23, wherein a concentration of the pharmaceutical composition in plasma reaches a maximum level 20 to 28 hours after a single administration.

31. The method of claim 23, wherein a concentration of the pharmaceutical composition in plasma reaches a maximum level about 24 hours after a single administration.

32. A method of treating effects of guanidinoacetate (GAA) toxicity, comprising administering to a subject in need thereof a pharmaceutical composition comprising a therapeutic amount of an arginine depleting enzyme, wherein the arginine depleting enzyme is a human arginase enzyme, a human arginine deiminase enzyme, or a combination thereof.

33. A method of treating a deficiency in guanidinoacetate methyltransferase (GAMT) activity in a subject, comprising administering to said subject a pharmaceutical composition comprising a therapeutic amount of an arginine depleting enzyme in combination with ornithine supplementation, wherein the arginine depleting enzyme is a human arginase enzyme, a human arginine deiminase enzyme, or a combination thereof.

34. The method of claim 33, the pharmaceutical composition comprises a high-dose L-ornithine supplementation.

35. The method of claim 33, comprising orally administering L-ornithine aspartate or L-ornithine hydrochloride.

* * * * *